United States Patent [19]

Hiraoka et al.

[11] Patent Number: 5,251,980
[45] Date of Patent: Oct. 12, 1993

[54] SENSING SYSTEM FOR MEASURING SPECIFIC VALUE OF SUBSTANCE TO BE MEASURED BY UTILIZING CHANGE IN THERMAL RESISTANCE

[75] Inventors: Jun Hiraoka; Setsuo Kodato, both of Atsugi; Yoshinobu Naitoh, Odawara, all of Japan

[73] Assignee: Anritsu Corporation, Tokyo, Japan

[21] Appl. No.: 920,484

[22] PCT Filed: Dec. 13, 1991

[86] PCT No.: PCT/JP91/01711

§ 371 Date: Aug. 10, 1992

§ 102(e) Date: Aug. 10, 1992

[87] PCT Pub. No.: WO92/10742

PCT Pub. Date: Jun. 25, 1992

[30] Foreign Application Priority Data

Dec. 14, 1990 [JP] Japan .................. 2-410875
Apr. 23, 1991 [JP] Japan .................. 3-119261

[51] Int. Cl.⁵ .................. G01N 25/00; G01N 25/18
[52] U.S. Cl. .................. 374/7; 374/44
[58] Field of Search ........... 374/4, 5, 7, 43, 44, 374/112, 164, 165, 179, 183, 185

[56] References Cited

U.S. PATENT DOCUMENTS

| | | |
|---|---|---|
| 2,852,850 | 9/1958 | Martin .................. 374/7 |
| 3,045,473 | 7/1962 | Hager, Jr. .................. 374/44 |
| 3,258,957 | 7/1966 | Smart .................. 374/164 |
| 3,279,239 | 10/1966 | Arends et al. .................. 374/44 |
| 4,236,403 | 12/1980 | Poppendiek .................. 374/44 |
| 4,630,938 | 12/1986 | Piorkovaska-Palczewska et al. .................. 374/44 |
| 4,766,008 | 8/1988 | Kodato . |
| 5,108,193 | 4/1992 | Furubayashi .................. 374/164 |
| 5,112,136 | 5/1992 | Sakuma et al. .................. 374/44 |

FOREIGN PATENT DOCUMENTS

| | | |
|---|---|---|
| 0144630 | 7/1985 | European Pat. Off. . |
| 49-70672 | 7/1974 | Japan . |
| 53-107382 | 9/1978 | Japan . |
| 57-39364 | 3/1982 | Japan . |
| 57-19640 | 4/1982 | Japan . |
| 59-45098 | 11/1984 | Japan . |
| 61-169752 | 7/1986 | Japan . |
| 63-179266 | 7/1988 | Japan . |
| 64-13445 | 1/1989 | Japan . |
| 2285241 | 11/1990 | Japan .................. 374/44 |
| WO89/08837 | 9/1989 | PCT Int'l Appl. . |
| 2182152 | 10/1986 | United Kingdom . |

Primary Examiner—William A. Cuchlinski, Jr.
Assistant Examiner—G. Bradley Bennett
Attorney, Agent, or Firm—Frishauf, Holtz, Goodman & Woodward

[57] ABSTRACT

This invention provides a sensing system for measuring a specific value such as the thickness, thermal conductivity, or the like of a substance to be measured by utilizing a change in thermal resistance with a simple arrangement. A sensor has a temperature difference setting thin film (202) and a temperature difference detection thin film (203) formed on a substrate (201) made of a thermally poor conductor, converts a change in temperature difference of the substrate (201) before and after a substance (200) to be measured is thermally coupled to the substrate into a change in thermal resistance of the substrate (201), and outputs the change in thermal resistance as a temperature difference information signal for calculating a desired specific value of the substance to be measured. A sensing device includes an arithmetic circuit (209) for converting the change in temperature difference of the substrate output from the sensor as the temperature difference information signal into the change in thermal resistance of the substrate, and calculating a desired specific value of the substance to be measured according to the converted change in thermal resistance and known information of the substance to be measured. A sensing method includes the step of providing a temperature difference to the substrate, the step of detecting a first temperature difference in the substrate in a state wherein the substance to be measured is not thermally coupled to the substrate, the step of detecting a second temperature difference in the substrate in a state wherein the substance to be measured is thermally coupled to the substrate, and the step of converting the first and second temperature differences into a thermal resistance of the substrate, and (Abstract continued on next page.)

calculating a desired specific value of the substance to be measured. According to the sensing system of this invention, the substance to be measured need only be thermally coupled to the substrate of the sensor, so that a desired specific value of the substance to be measured can be easily and precisely measured.

20 Claims, 34 Drawing Sheets

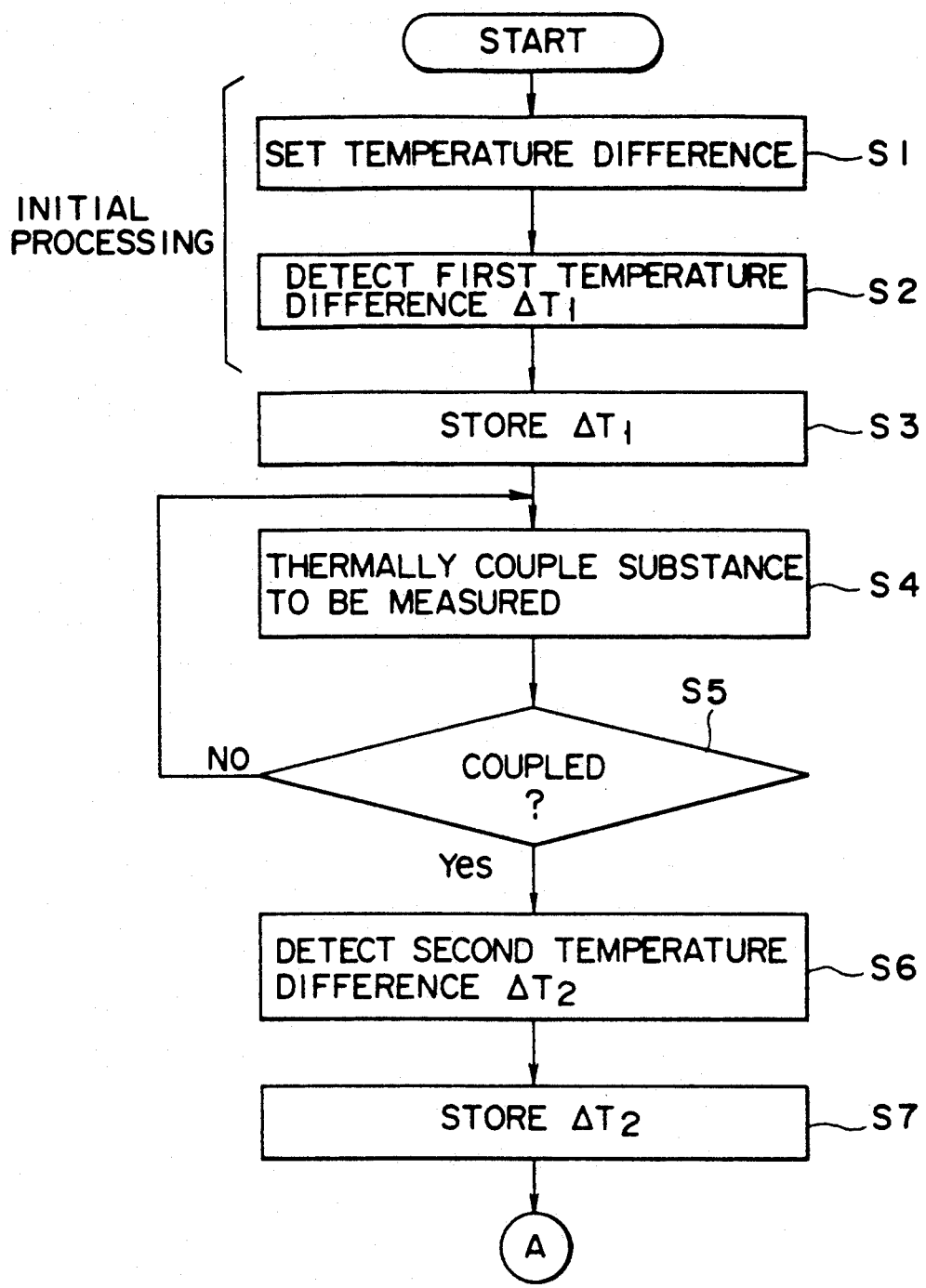
F I G. 3A-1

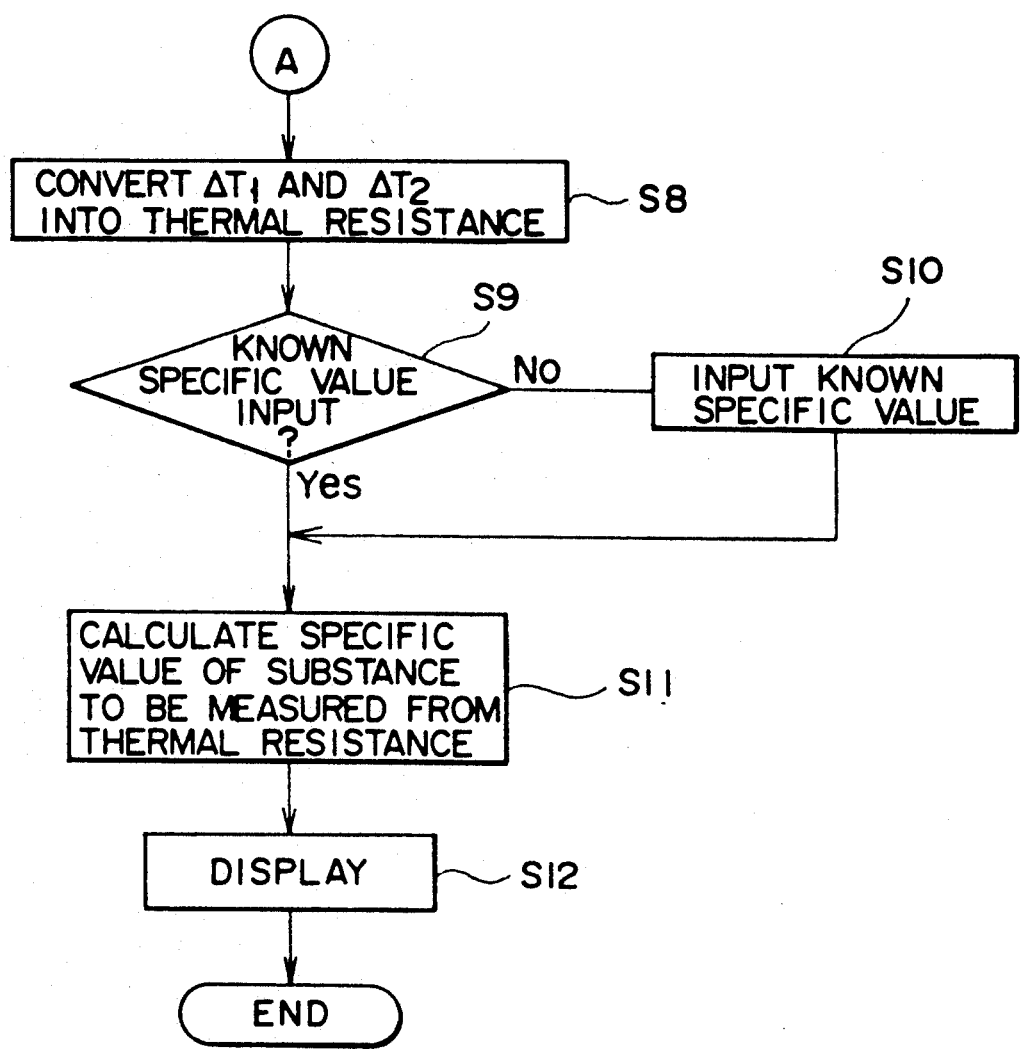
FIG. 3A-II

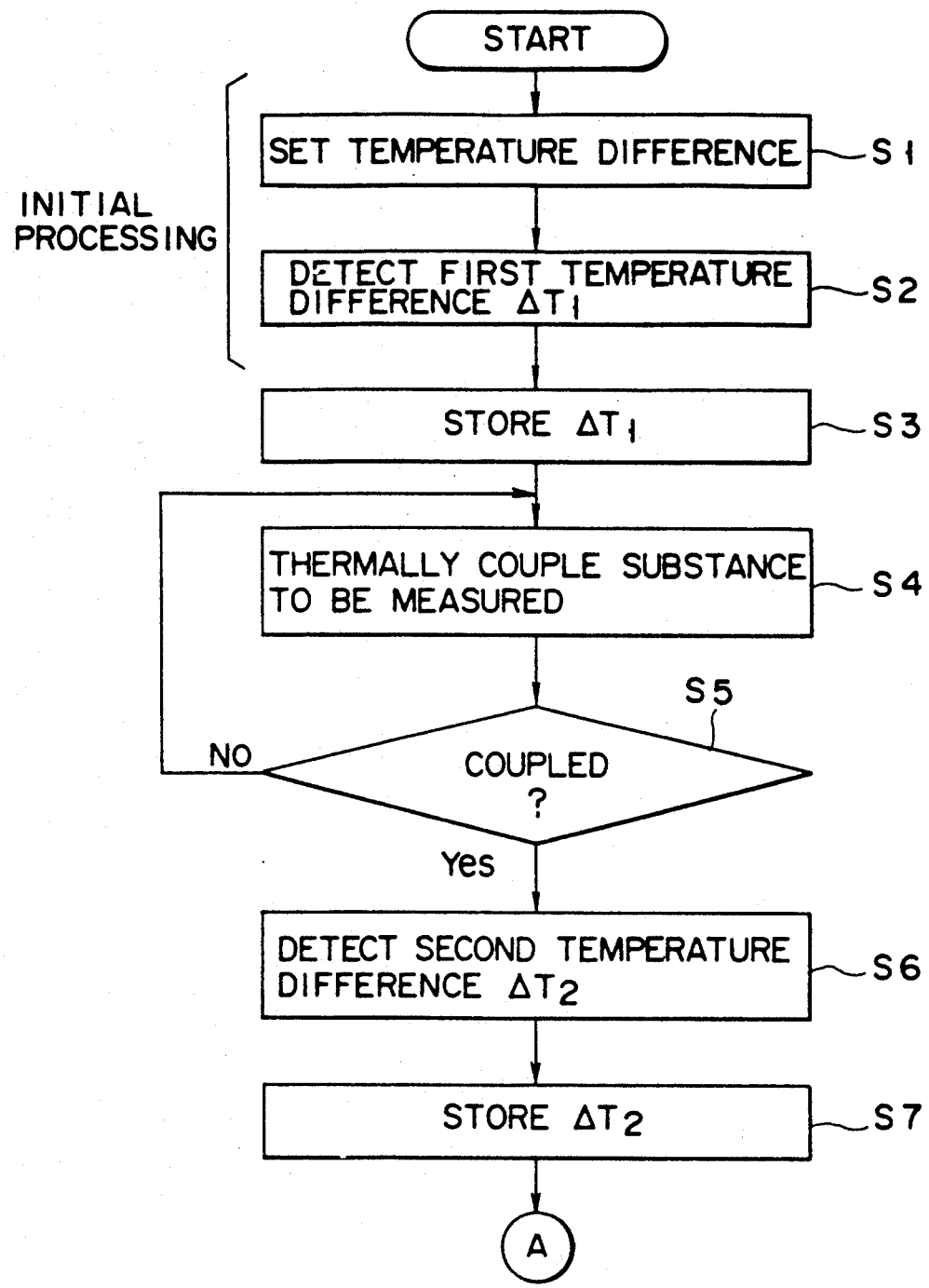
F I G. 3B-I

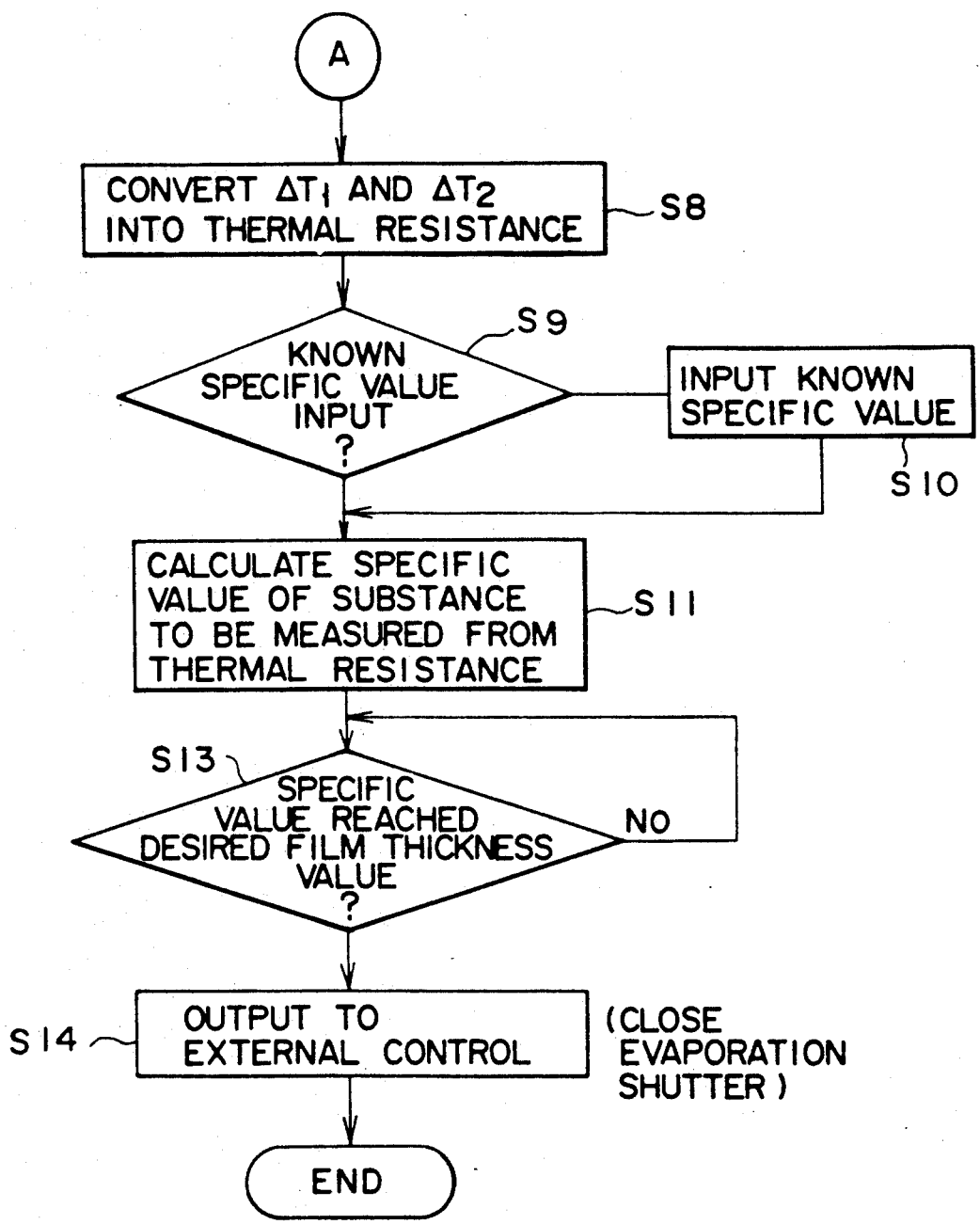
FIG. 3B-II

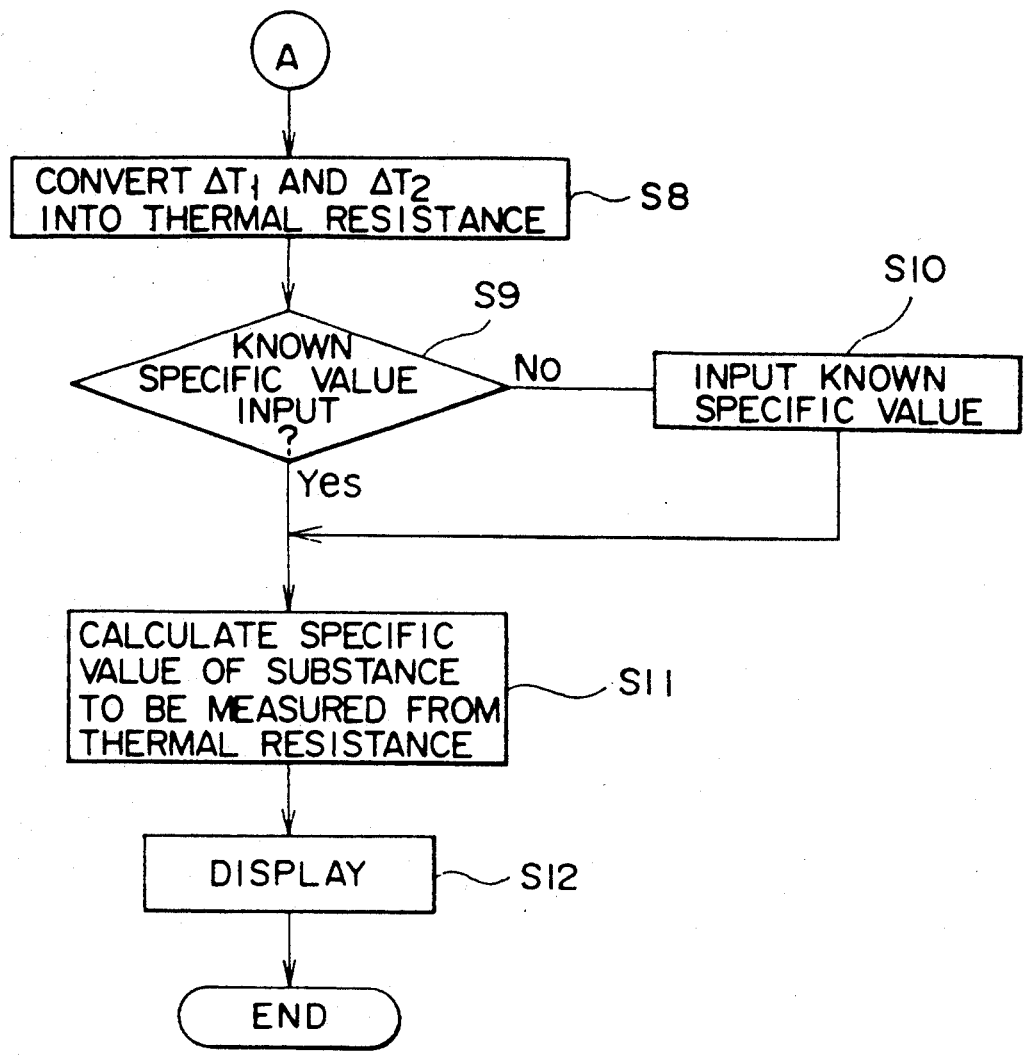
FIG. 3C-II

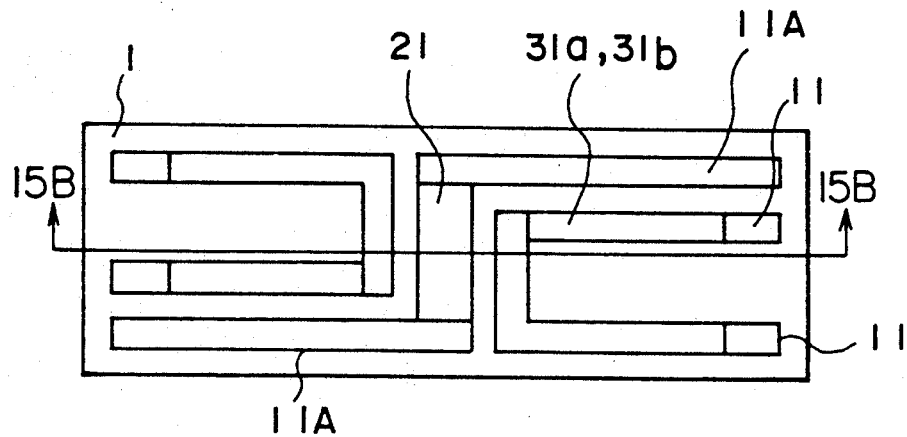
F I G. 15A
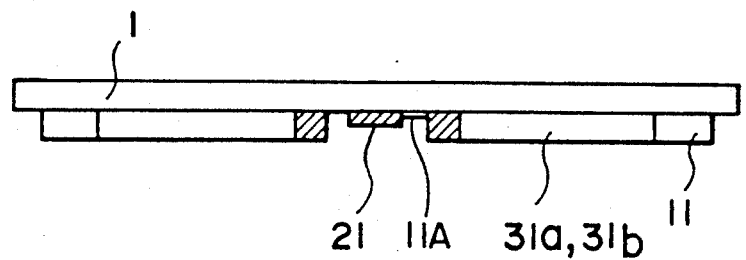
F I G. 15B

SENSING SYSTEM FOR MEASURING SPECIFIC VALUE OF SUBSTANCE TO BE MEASURED BY UTILIZING CHANGE IN THERMAL RESISTANCE

TECHNICAL FIELD

The present invention relates to a sensing system for measuring a specific value such as the thickness, thermal conductivity, or the like of a substance to be measured and, more particularly, to a sensing system applicable to measurements of specific values such as the thicknesses and thermal conductivities of various substances to be measured, the concentration of a liquid, and the like, including measurements of the film thicknesses of evaporated/adhered/deposited substances in a vacuum evaporation apparatus, a plasma CVD apparatus, a sputtering apparatus, and the like, and the plating thickness upon Au plating.

BACKGROUND ART

Conventionally, a quartz type film thickness detector is used in a film thickness measurement of an adhered/deposited substance to be evaporated in a vacuum evaporation apparatus, a plasma CVD apparatus, a sputtering apparatus, and the like. The quartz type film thickness detector utilizes a phenomenon that the resonance frequency of a quartz oscillator changes according to the thickness of an evaporated film, and has features such as high detection precision and a high response speed.

In recent years, an electron impact excitation spectroscopy, which utilizes excited light upon electron impact of an evaporating metal, tends to be used in such a film thickness measurement. The film thickness measurement based on the electron impact excitation spectroscopy utilizes the following phenomenon. When a thermoelectron is caused to collide against the vapor flow of an evaporating substance to excite the evaporating substance, light having a wavelength spectrum inherent to the substance is emitted, and the light intensity at that time is proportional to the density of the vapor flow, i.e., the evaporation rate. In particular, this film thickness measurement has a feature that the film thickness of a two-element simultaneous evaporated film can be detected by providing an optical filter to a detection unit.

As another prior art, an amorphous semiconductor thin film having a large Seebeck coefficient, which can be utilized as a temperature sensor or a strain sensor, has been reported (U.S. Pat. No. 4,766,008, and Published Unexamined Japanese Patent Application No. 62-47177).

As a conventional method of detecting thermal conductivity, a method of measuring the thermal conductivity of a substance by bringing a thermal conductivity detection element into contact with the substance to be measured is adopted (Published Unexamined Japanese Patent Application No. 49-70672). More specifically, the thermal conductivity detection element is brought into tight contact with a substance to be measured, and a cyclic current is flowed through the thermal conductivity detection element to cause endothermic and exothermic reactions in a surface of the thermal conductivity detection element, which surface is in tight contact with the substance to be measured. At the same time, the temperature of the surface of the thermal conductivity detection element, which surface is in tight contact with the substance to be measured, is measured to detect a delay of a phase or a difference in amplitude ratio of the measured temperature waveform with respect to the current waveform flowed through the thermal conductivity detection element due to the thermal physical property of the substance to be measured. Thus, the thermal conductivity of the substance to be measured is measured using the density and specific heat values of the substance to be measured, which are obtained beforehand by some method. This method has a merit that a measurement apparatus is relatively light in weight.

As another thermal conductivity measurement method, a method of measuring the thermal conductivity of a substance to be measured by sandwiching the substance to be measured between substrates respectively having low and high thermal conductivities is also adopted (Published Unexamined Japanese Patent Application No. 53-107382). More specifically, on the substrate having the low thermal conductivity, a heat generating means, and a temperature measuring means located near the heat generating means are arranged. A substance to be measured is sandwiched between the substrates respectively having the low and high thermal conductivities, and when heat from the heat generating means is conducted through the substance to be measured, a change in temperature near the heat generating means is detected by the temperature measuring means, thereby measuring the thermal conductivity of the substance to be measured. This measurement method has the following merit. That is, since temperatures obtained when a substance to be measured is sandwiched and not sandwiched need only be measured, the thermal conductivity of the substance to be measured can be measured within a relatively short period of time.

In this manner, methods of measuring the thermal conductivity of a substance to be measured by utilizing thermal conduction are widely known, and can be utilized in the above-mentioned thickness measurement of a substance to be measured since their application range is wide.

However, these prior arts respectively have the following problems.

(1) The film thickness measurement based on the quartz type resonance frequency method requires a stable frequency oscillator and frequency counter, and the quartz oscillator cannot be rendered compact. For this reason, it is difficult to attain miniaturization and integration of a film thickness detector. Furthermore, this measurement is easily influenced by high-frequency noise, and is complex in procedure.

(2) The film thickness measurement based on the electron impact excitation spectroscopy requires a high-sensitive light-receiving element and a thermoelectron emitter, and results in a very expensive system. In addition, since a detection unit comprises a light-emitting element, it is difficult to attain miniaturization and integration. Furthermore, a measurement method is complex in procedure.

(3) As for the amorphous semiconductor thin film having the large Seebeck coefficient, no concrete disclosure of a thickness sensor utilizing a change in thermal resistance as the subject of the present invention is available.

(4) As a practical problem, when a measurement of the thermal conductivity of a substance is utilized in a thickness measurement of a substance, objects to be measured widely vary including, e.g., constructions, gas piping systems, structures, and the like. Thus, it is difficult to meet requirements such as an inspection of the degree of progress of deterioration or corrosion of such objects, a measurement of the thickness of an asphalt, and the like.

(5) More specifically, in the method wherein the thermal conductivity detection element is brought into tight contact with a substance to be measured to measure the thermal conductivity of the substance to be measured, the density and specific heat values of the substance to be measured must be measured beforehand by some method. When the density and specific heat values of the substance to be measured cannot be obtained, the thermal conductivity of the substance to be measured cannot be measured.

(6) In this method, in the method wherein a substance to be measured is sandwiched between the substrates respectively having the high and low thermal conductivities to measure the thermal conductivity of the substance to be measured, a measurement apparatus cannot be formed on a single plane, and furthermore, samples to be measured must be prepared. In addition, since the substance to be measured must be sandwiched upon measurement, the measurement is not easy.

(7) When the thickness of a substrate to be used is small or when a substance to be measured having a low thermal conductivity is to be measured, since the dimensions of the thermal conductivity detection element are large, and the thermal resistance is inevitably increased, sensitivity is poor, and measurement precision is limited. In addition, since the thermal conductivity element has a low response speed, the measurement time is prolonged.

(8) In order to measure a liquid concentration, e.g., an alcohol concentration in water, a method utilizing a change in refractive index is used. However, this method can only measure a concentration up to 30%. In addition, in a method using a platinum wire as a bolometer, the apparatus becomes too large.

DISCLOSURE OF INVENTION

It is, therefore, the first object of the present invention to provide a sensor, which has features such as easy miniaturization and integration, a simple measurement, a high resistance to the influence of high-frequency noise, and an inexpensive structure, and can measure specific values such as the thickness and thermal conductivity of a substance to be measured, the concentration of a liquid, and the like.

It is the second object of the present invention to provide a sensing apparatus, which has features such as easy miniaturization and integration, a simple measurement, a high resistance to the influence of high-frequency noise, and an inexpensive structure, and can measure specific values such as the thickness and thermal conductivity of a substance to be measured, the concentration of a liquid, and the like.

It is the third object of the present invention to provide a sensing method, which has features such as easy miniaturization and integration, a simple measurement, a high resistance to the influence of high-frequency noise, and an inexpensive structure, and can measure specific values such as the thickness and thermal conductivity of a substance to be measured, the concentration of a liquid, and the like.

It is still another object of the present invention to provide a sensor, which can increase the response speed, and can improve measurement precision in addition to the first object.

According to the first aspect of the present invention, there is provided a sensor comprising:
- a substrate at least a portion of which can be thermally coupled to a substance to be measured, and which is formed of a thermally poor conductor;
- a temperature difference setting thin film formed on the substrate to provide a temperature difference to the substrate;
- a temperature difference detection thin film formed on the substrate to detect a change in temperature difference provided by the temperature difference setting thin film;
- first electrode means, formed on the substrate, for supplying a predetermined electrical power to the temperature difference setting thin film; and
- second electrode means, formed on the substrate, for outputting an output from the temperature difference detection thin film, and
- wherein a change in temperature difference provided to the substrate before and after the substance to be measured is thermally coupled to the substrate is converted into a change in thermal resistance of the substrate, and the change in thermal resistance of the substrate is output as a temperature difference information signal for calculating a desired specific value of the substance to be measured.

According to the second aspect of the present invention, there is provided a sensing device comprising:
- a substrate at least a portion of which can be thermally coupled to a substance to be measured, and which is formed of a thermally poor conductor;
- temperature difference setting means for providing a temperature difference to the substrate;
- temperature difference detection means for detecting a change in temperature difference provided by the temperature difference setting means;
- temperature difference/thermal resistance conversion means for converting, into a change in thermal resistance of the substrate, the change in temperature difference detected by the temperature difference detection means before and after the substance to be measured is thermally coupled to the substrate; and
- specific value calculation means for calculating a desired specific value of the substance to be measured according to the change in thermal resistance converted by the temperature difference/thermal resistance conversion means, and known value information of the substance to be measured.

According to the third aspect of the present invention, there is provided a sensing method comprising the steps of:
- setting a temperature difference in a substrate at least a portion of which can be thermally coupled to a substance to be measured;
- detecting a first temperature difference in the substrate in a state wherein the substance to be measured is not thermally coupled to the substrate;
- thermally coupling the substrate to the substance to be measured;
- detecting a second temperature difference in the substrate in a state wherein the substance to be measured is thermally coupled to the substrate;
- converting the first and second temperature differences into a thermal resistance of the substrate; and
- calculating a specific value of the substance to be measured according to the converted thermal resistance and known information of the substance to be measured.

According to the fourth aspect of the present invention, there is provided a sensor wherein a groove for decreasing the thickness of the portion to be thermally coupled to the substance to be measured is formed in the substrate in addition to features of the first aspect.

BRIEF DESCRIPTION OF DRAWINGS

FIGS. 3A to 3C are flow charts for exemplifying different operation flows of FIG. 2;

FIGS. 15A and 15B are views showing a sensor according to the ninth embodiment;

BEST MODE OF CARRYING OUT THE INVENTION

The present invention will be schematically described below with reference to FIG. 1, which shows the basic arrangement of a sensing system according to the present invention.

Figure 1:
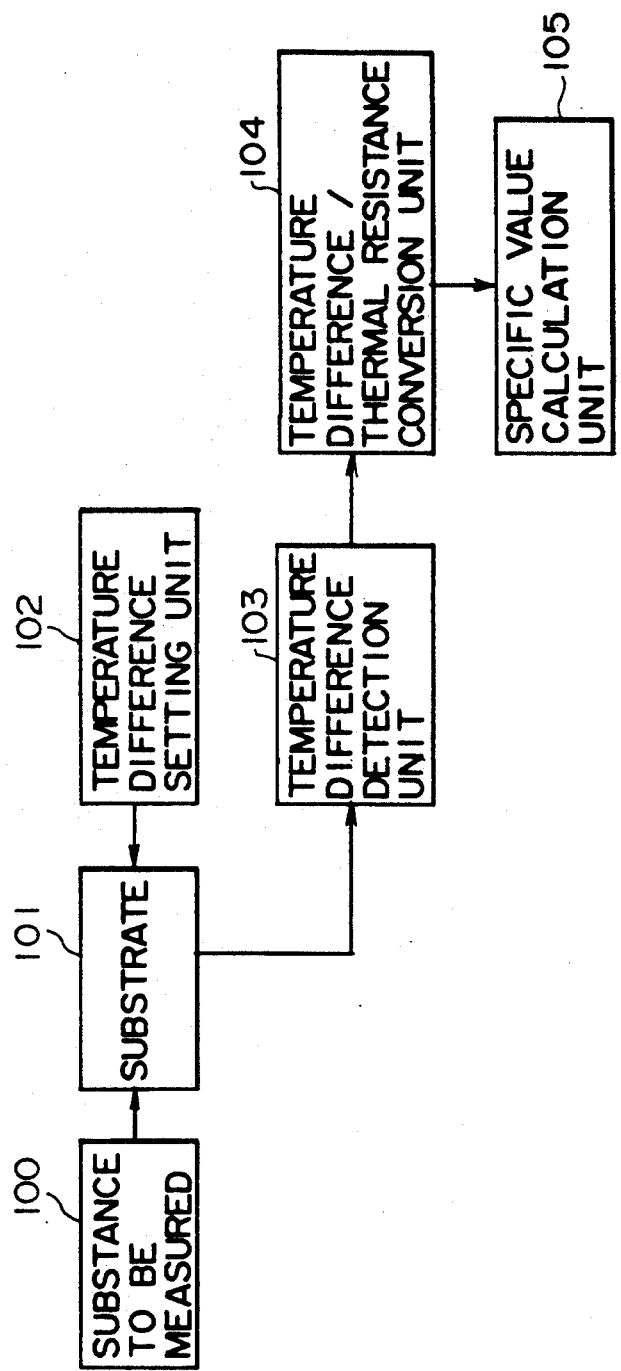
FIGS. 1 and 2 are block diagrams showing the basic arrangements of sensing systems according to the present invention, respectively.

In FIG. 1, a substrate 101 formed of a thermally poor conductor, and having an area of several mm$^2$ is coupled to a temperature difference setting unit 102 for internally or externally setting a temperature difference in the substrate 101, and is also coupled to a temperature difference detection unit 103 for internally or externally detecting a temperature difference generated in the substrate 101.

The output terminal of the temperature difference detection unit 103 is connected to a signal processing unit 105 for calculating a desired specific value of a substance to be measured through a temperature difference/thermal resistance conversion unit 104.

In this arrangement, when the substrate 101 is thermally coupled to a substance 100 to be measured, a temperature difference set in the substrate 101 changes from $\Delta T_1$ to $\Delta T_2$ before and after the coupling. More specifically, this change indicates that the synthesized thermal resistance of the substrate 101 and the substance 100 to be measured changes due to coupling of the substance 100 to be measured depending on the shape, thermal conductivity, and thermal resistance of the substance 100 to be measured.

Thus, the output from the temperature difference detection unit 103 is supplied to the temperature difference/thermal resistance conversion unit 104, and is converted into a thermal resistance. Thereafter, the converted thermal resistance is processed by the signal processing unit 105 together with known information of the substance 100 to be measured on the basis of a change in thermal resistance before and after the coupling of the substance 100 to be measured according to a predetermined equation (to be described later), thus calculating an unknown specific value of the substance 100 to be measured.

For example, if the width and length of the substance 100 to be measured and its thermal conductivity are given as known information, the thickness of the substance 100 to be measured can be calculated based on these pieces of information and the change value of the synthesized thermal resistance according to the predetermined equation. Contrary to this, if the width and length of the substance 100 to be measured and its thickness are given as known information, the thermal conductivity of the substance 100 to be measured can be calculated based on these pieces of information and the change value of the synthesized thermal resistance.

Figure 2:
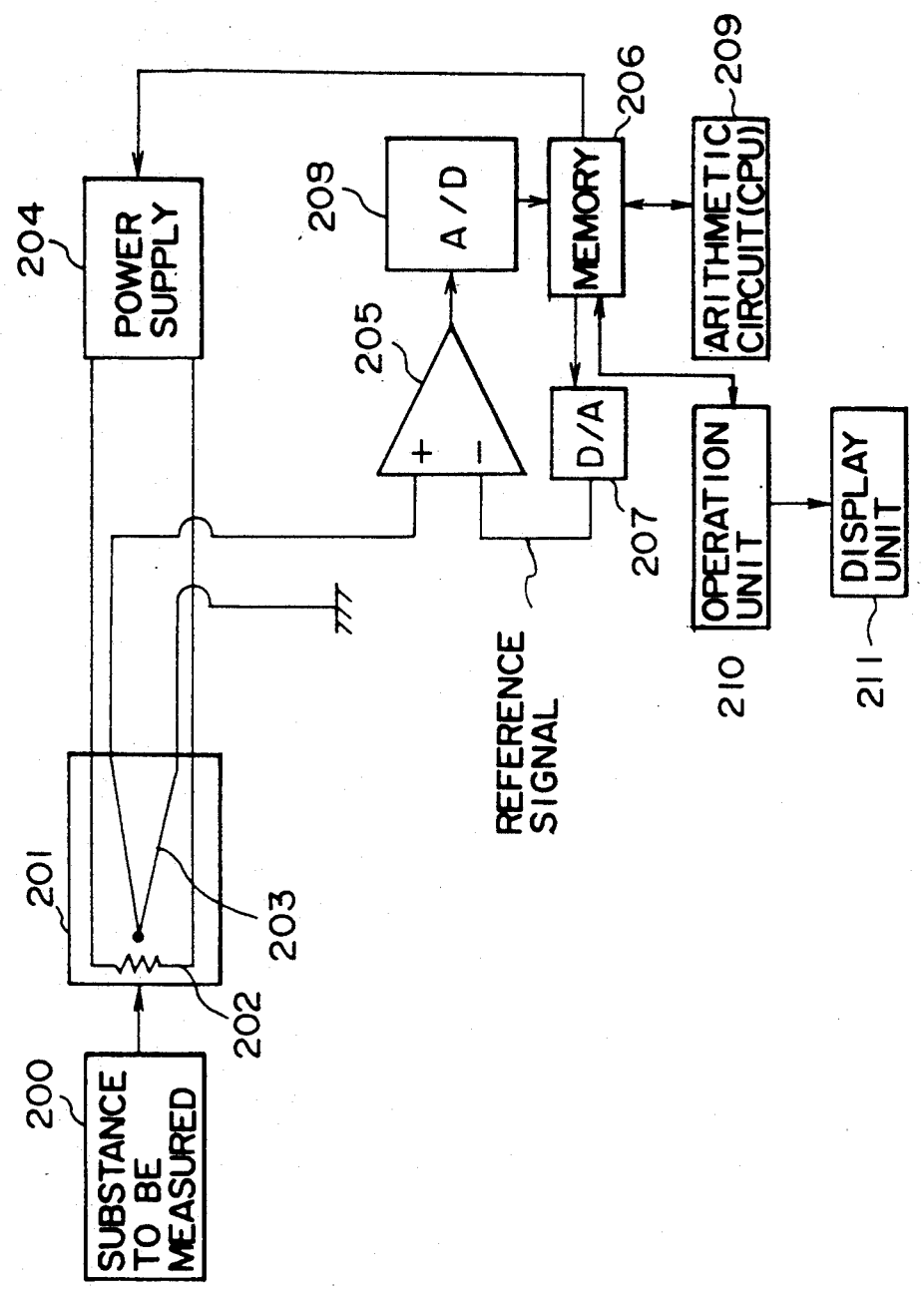

FIG. 2 shows the arrangement shown in FIG. 1 in more detail. A temperature difference setting thin film 202 comprising, e.g., a thin film heater element for heating, a thin film Peltier element for cooling, or the like, as a means corresponding to the above-mentioned temperature difference setting unit 102, and a temperature difference detection thin film 203 comprising, e.g., a thin film thermocouple element, a thin film thermistor, or the like, as a means corresponding to the above-mentioned temperature difference detection unit 103, are formed on a substrate 201.

The temperature difference setting thin film 202 is connected to a power supply 204 for applying a predetermined electric power to the thin film 202 to perform heating or cooling, thereby giving a temperature difference to the substrate 201.

One end of the temperature difference detection thin film (in this case, a thin film thermocouple element) 203 is grounded, and the other end thereof is connected to one input terminal of a differential amplifier 205. The other input terminal of the differential amplifier 205 receives a reference (temperature) signal from a memory 206 through a D/A converter 207, and the output terminal thereof is connected to the memory 206 through an A/D converter 208.

The memory 206 is connected to an arithmetic circuit (to be referred to as a CPU hereinafter) 209 for controlling the overall system, and performing the above-mentioned temperature difference/thermal resistance conversion, and calculation of a desired specific value of the substance to be measured, and is also connected to the power supply 204 and an operation unit 210 having, e.g., a function of inputting the above-mentioned known information of the substance to be measured. The operation unit 210 is connected to a display unit 211 for displaying a desired specific value (e.g., the thickness or thermal conductivity) of the substance to be measured calculated by the CPU 209 through the memory 206.

The operation of the above-mentioned arrangement is basically the same as that shown in FIG. 1. In this case, temperature difference information given as a thermoelectromotive force from the temperature difference detection thin film 203 is converted into a digital signal, and the digital signal is processed. Note that the reference (temperature signal) supplied from the memory 206 to the differential amplifier 205 is a value corresponding to a cold junction potential for obtaining the thermoelectromotive force.

FIG. 3A shows a general (basic) operation flow of the sensing system according to the arrangement shown in FIG. 2.

More specifically, in step S1, in order to set a temperature difference in the substrate 201, the CPU 209 drives the power supply 204 through the memory 206 to flow a predetermined electric power, i.e., a current through the temperature difference setting thin film 202, thereby heating or cooling a predetermined portion of the substrate 201. In step S2, a first temperature difference $\Delta T_1$ is detected. In step S3, in order to store the detected temperature difference, the CPU 209 instructs the memory 206 to fetch temperature difference information converted into a digital signal through the temperature difference detection thin film 203, the differential amplifier 205, and the A/D converter 207. Steps S1 to S3 correspond to initial processing.

Next, when a substance 200 to be measured is thermally coupled to the substrate 201 in step S4, the CPU 209 judges the coupling state in step S5, and thereafter, instructs to detect and store a second temperature difference $\Delta T_2$ in the same manner as in the above-mentioned first temperature difference $\Delta T_1$ in steps S6 and S7.

Subsequently, the CPU 209 converts the first and second temperature differences $\Delta T_1$ and $\Delta T_2$ into thermal resistances in step S8, and judges the input state of a known specific value (information) of a substance 212 to be measured in steps S9 and S10. Thereafter, the CPU 209 calculates a desired specific value of the substance 200 to be measured on the basis of the thermal resistances and the known information in step S11, and instructs to display the calculated specific value on the display unit 211.

Figures 1, 3C:
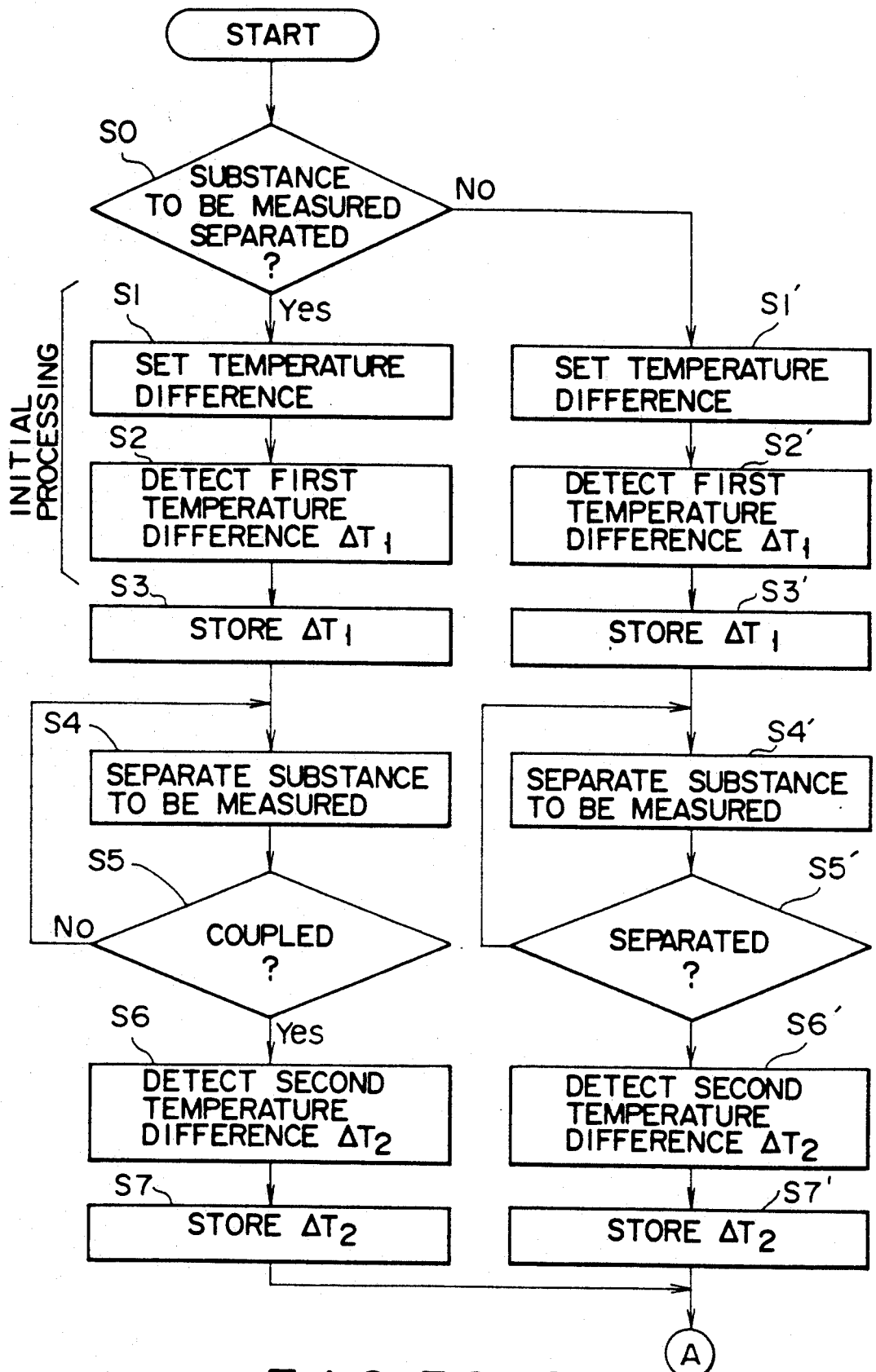

FIGS. 3B and 3C show operation flows when the sensing system of the present invention is applied to an evaporation monitor and a heat sensor, and operations according to FIG. 3A are performed.

In FIG. 2, the substrate 201, and the temperature difference setting thin film 202 and the temperature difference detection thin film 203 which are formed on the substrate 201, constitute a sensor in the present invention.

In the above description, temperature difference change values $\Delta T_1$ and $\Delta T_2$ of the substrate before and after thermal coupling of a substance to be measured to the substrate are directly converted into changes in thermal resistance, thereby calculating a desired specific value of the substance to be measured.

However, the present invention is not limited to the aspect as described above. A current (i.e, a heat generating amount or cooling amount) to be applied to the temperature difference setting thin film 202 is controlled to eliminate any difference between $\Delta T_1$ and $\Delta T_2$, i.e., to attain $\Delta T_1 = \Delta T_2$, and the corresponding current values $I_1$ and $I_2$ (heat generating amounts $Q_1$ and $Q_2$) may be converted into changes in thermal resistance of the substrate (a detailed description thereof will be made later).

Some detailed embodiments of the present invention will be described below on the basis of the above-mentioned summary.

Figure 4A:
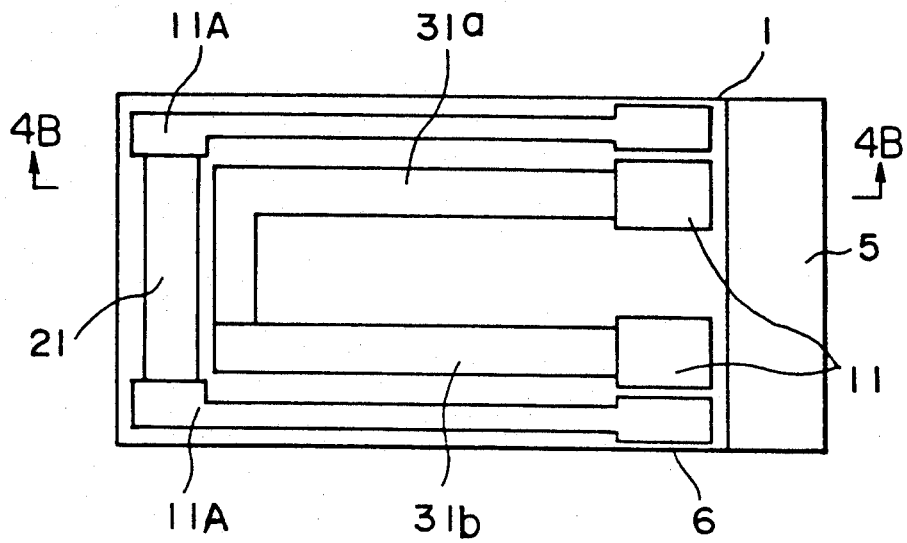
FIGS. 4A to 4C are views showing a structure of a sensor according to the first embodiment of the present invention.
Figure 4B:
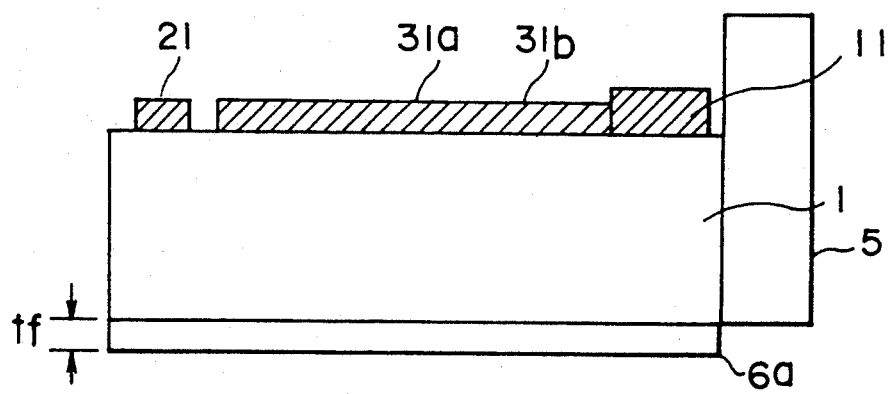

The detailed structure of a sensor will be described below with reference to FIGS. 4A, 4B, and 4C.

This sensor is constituted by a thermally poor conductor substrate 1, a portion of which is thermally connected to a heat sink 5, a temperature difference setting thin film 2 for heating or cooling a predetermined position of the substrate 1, and a temperature difference detection thin film 3 for detecting the temperature at a desired position on the substrate heated or cooled by the temperature difference setting thin film 2 for heating or cooling. In this embodiment, a thin film heater 21 for heating and thin film thermocouples 31a and 31b for temperature detection are formed on the thermally poor conductor substrate 1, which is thermally connected to the heat sink 5. As a material of the thermally poor conductor substrate 1, since it is preferable that the thermal resistance largely changes for a small film thickness of an adhered layer 6a as a substance to be measured, the material suitably has a thermal conductivity smaller than that of the adhered layer 6a. For this reason, as the material of the thermally poor conductor substrate 1, glass, ceramic, quartz, crystal, alumina, or an organic film of, e.g., epoxy, polyimide, or the like is used.

In order to heat the predetermined position on the substrate 1, for example, absorption heating to a light absorption layer by light is known in addition to resistive heating by electricity. In this embodiment, heating is performed using the thin film heater 21. On the other hand, in order to cool the predetermined position on the substrate, cooling by, e.g., a Peltier effect element using, e.g., a compound of bismuth or tellurium, is known. To summarize, in the sensor according to the present invention, a predetermined position on the substrate 1 need only be heated or cooled.

In order to detect the temperature at a desired position on the substrate 1, a thermocouple, a radiation thermometer, and the like are known. In this embodiment, the temperature is detected using the thin film thermocouples 31a and 31b, and an ohmic electrode 11 (to be simply referred to as an electrode 11 hereinafter) for detecting a potential difference therebetween.

In this embodiment, as described above, a portion of the thermally poor conductor substrate 1 is thermally connected to the heat sink 5. The heat sink 5 may comprise a block-like member having a large heat capacity, or may be constituted by connecting a thin conductor wire, which can conduct heat well to an external portion. When the substrate 1 is connected to the heat sink 5, a portion of the thermally poor conductor substrate 1 is maintained at a constant temperature (this portion will be referred to as a thermostatic portion hereinafter). The thermostatic portion 6 is located at a position opposite to the thin film heater 21, i.e., the right peripheral portion (a portion indicated by B in FIG. 4C) in the substrate 1 in FIGS. 4A and 4B. In this case, since the thermostatic portion 6 is arranged in the heat sink 5 such as a Cu block, its temperature is always maintained at a constant temperature regardless of the ON/OFF state of the thin film heater 21. The thermostatic portion 6 is required for a cold junction of the thin film thermocouples 31a and 31b. However, a temperature gradient (difference) need only be substantially formed in the substrate 1 when a predetermined position on the substrate 1 is heated or cooled. In FIG. 4A, in order to eliminate radiation of heat conducted from the thin film heater 21 through heater electrodes, i.e., to improve heating efficiency, a portion of each electrode 11A for the thin film heater 21 has a thin wiring pattern.

A manufacturing method of the sensor shown in FIGS. 4A and 4B (FIG. 4B being a sectional view taken along line 4B—4B of FIG. 4A) will be briefly described below.

As the thermally poor conductor substrate 1, as described above, glass, ceramic, quartz, crystal, alumina, or an organic film of, e.g., epoxy, polyimide, or the like is used. The substrate 1 is sufficiently washed using, e.g., an organic solvent, and thereafter, is dried in a clean environment.

The thin film thermocouples 31a and 31b are formed on the substrate 1. The thin film thermocouples 31a and 31b preferably have a large Seebeck coefficient, and comprise an amorphous semiconductor thin film such as amorphous silicon (a-Si) or amorphous germanium (a-Ge). These amorphous semiconductors are deposited on the substrate 1 by the plasma CVD method using a gas such as $SiH_4$, $GeH_4$, $H_2$, or the like. At this time, the supply amount of a doping gas such as $PH_3$ or $AsH_3$ for an n-type semiconductor or $B_2H_6$ for a p-type semiconductor is often varied. An unnecessary portion of the deposited amorphous semiconductor is removed by the photoetching technique to form the predetermined thin film thermocouples 31a and 31b. Note that the thin film thermocouples 31a and 31b may comprise an amorphous thin film having a large Seebeck coefficient, or the like, and a metal thin film having a small Seebeck coefficient, or the like.

Subsequently, the thin film heater 21 is formed on the substrate 1. As the thin film resistor, a metal thin film of, e.g., nichrome, tantalum, or the like is used. These metal thin films are deposited on the substrate 1 by the sputtering method or vacuum evaporation method. An unnecessary portion of this metal thin film is removed by the photoetching technique to for the thin film heater 21 having a desired pattern.

Furthermore, an electrode metal thin film such as Au is deposited, and its unnecessary portion is removed by the photoetching technique to form electrodes 11 and electrodes 11A for the thin film thermocouples 31a and 31b and the thin film heater 21.

Note that in some cases, an $SiO_2$ thin film, an $Si_3N_4$ thin film, or the like is formed as a surface protection film for the thin film thermocouples 31a and 31b and the thin film heater 21.

The measurement principle of the above-mentioned sensor and the role of the thermostatic portion 6 will be explained below with reference to FIG. 5.

Figure 4C:
Figure 5:
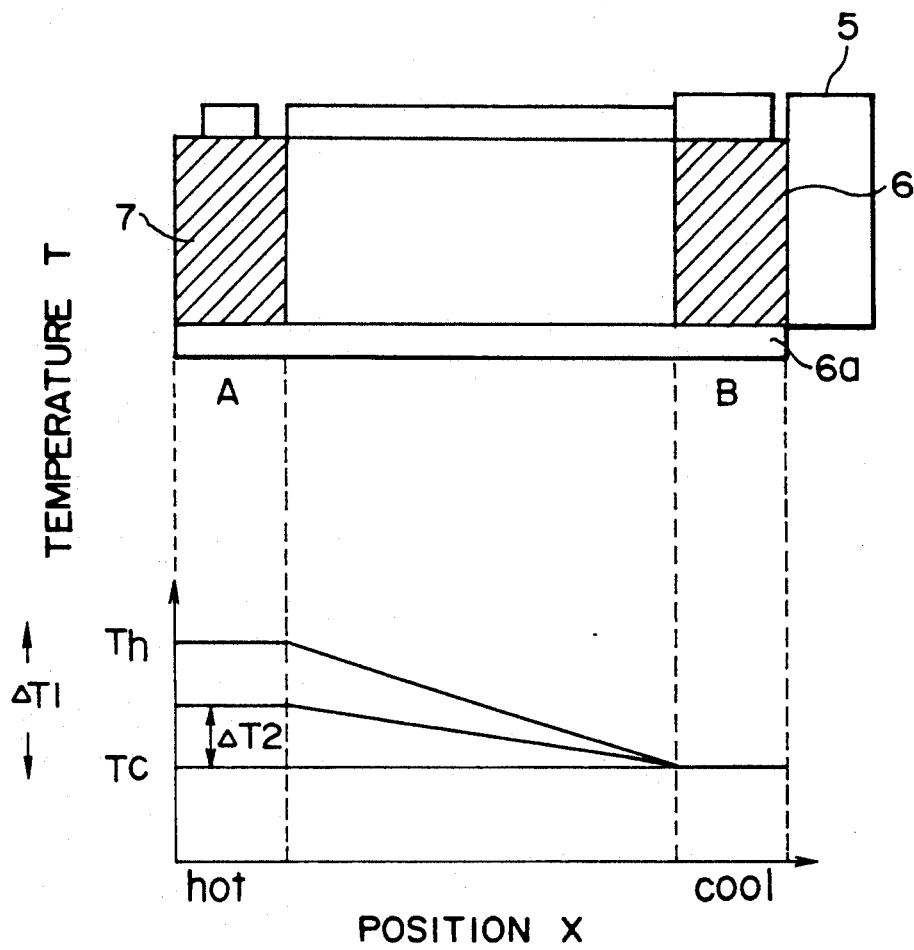
FIG. 5 is a view showing the measurement principle and the role of a thermostatic portion of the sensor shown in FIGS. 4A to 4C.

FIG. 5 is a view showing a temperature gradient in a process wherein the predetermined position on the substrate 1 is heated (only heating is performed since the thin film heater is used in this case) in the embodiment described above with reference to FIGS. 4A to 4C. In FIG. 5, since the thermostatic portion 6 (a peripheral portion B in the substrate indicated by right hatching in FIG. 5) is directly arranged in the heat sink 5 such as a Cu block, a constant temperature is always maintained regardless of the ON/OFF state of the thin film heater 21.

In contrast to this, a heated portion 7 at a desired position (a peripheral portion A in the substrate indicated by left hatching in FIG. 5; a portion indicated by A in FIG. 4C) has a temperature equal to that of the thermostatic portion 6 when the thin film heater 21 is OFF. However, when the thin film heater 21 is ON, a temperature difference $\Delta T_1$ is generated between the heated portion 7 and the thermostatic portion 6.

The temperature difference $\Delta T_1$ is obtained as a product of a heating amount Q of the thin film heater 21 and a resistance $R_s$, and is expressed by the following equation (1):

$$\Delta T_1 = Q \times R_s \tag{1}$$

In this case, the thermal resistance $R_s$ depends almost mainly on only the thermal resistance of the substrate 1. Therefore, as for the substrate 1, when the thermal conductivity is represented by $\lambda_s$, the length is represented by $L_s$, the width is represented by $W_s$, and the thickness is represented by $t_s$, the thermal resistance RS is given by the following equation (2):

$$R_s = \frac{1}{\lambda_s} \times \frac{L_s}{W_s \times t_s} \tag{2}$$

In this manner, when the adhered layer 6a is not present, i.e., in the process wherein the predetermined position on the substrate 1 is heated, the temperature difference $\Delta T_1$ becomes constant.

Subsequently, a process for detecting a first temperature after the desired position on the substrate 1 is heated is started. The temperature difference $\Delta T_1$ is detected using the thin film thermocouples 31a and 31b. At this time, a thermoelectromotive force $V_1$ of the thin film thermocouples 31a and 31b is obtained as a product of a Seebeck coefficient S of the thin film thermocouples 31a and 31b and the temperature difference $\Delta T_1$, as shown in the following equation (3):

$$V_1 = S \times \Delta T_1 \tag{3}$$

Since no adhered layer 6a is present at this time, the generated thermoelectromotive force $V_1$ is constant.

From this process, a process for forming the adhered layer 6a on at least a portion of the surface of the substrate 1 is started.

The adhered substance 6a, which can be measured by the present invention, can be any substances such as metals, e.g., Au, Pt, Ti, Cr, and the like, semiconductors such as Si, GaAs, ZnTe, and the like, or insulating materials such as $SiO_2$, $Si_3N_4$, $Al_2O_3$, and the like. This is because the thickness measurement of the adhered layer 6a utilizes a change in thermal resistance.

In this embodiment, the adhered layer 6a is formed on a surface opposing the surface on which the thin film heater 21 and the thin film thermocouples 31a and 31b are formed. Before the adhered layer 6a is formed, heat is conducted from the heated portion 7 to the thermostatic portion 6 while flowing through only the interior of the substrate 1. On the other hand, when the adhered layer 6a is formed, the heat flowing through only the interior of the substrate 1 is conducted from the heated portion 7 to the thermostatic portion 6 while partially flowing through the adhered layer 6a. For this reason, the thermal resistance between the heated portion 7 and the thermostatic portion 6 is decreased. As for the adhered layer 6a, when the thermal conductivity is represented by $\lambda_f$, the length is represented by $L_f$, the width is represented by $W_f$, and the thickness is represented by $t_f$, the thermal resistance $R_f$ of only the adhered layer 6a is expressed by the following equation (4):

$$R_f = \frac{1}{\lambda_s} \times \frac{L_f}{W_f \times t_f} \quad (4)$$

The synthesized thermal resistance R of the thermal resistance $R_s$ of the substrate 1 and the thermal resistance $R_f$ of the adhered layer is expressed by the following equation (5):

$$R = \left( \frac{1}{R_s} + \frac{1}{R_f} \right)^{-1} \quad (5)$$

Like in equation (4), a temperature difference $\Delta T_2$ between a heated portion 7 and the thermostatic portion 6 after the adhered layer 6a is formed is expressed by the following equation (6):

$$\Delta T_2 = Q \times R \quad (6)$$

As can be seen from equation (6), the temperature difference $\Delta T_2$ is decreased from the temperature difference $\Delta T_1$ before the adhered layer 6a is formed.

Subsequently, a process for detecting a second temperature at the predetermined position after the adhered layer 6a is formed is started. More specifically, in this embodiment, the temperature difference $\Delta T_2$ is measured. The detection method of the second temperature is the same as the detection method of the first temperature. In the embodiment shown in FIGS. 4A and 4B, the second temperature is detected based on the thermoelectromotive force by the thin film thermocouples 31a and 31b. At this time, a thermoelectromotive force $V_2$ is obtained in the same manner as equation (3) described above, and is given by the following equation (7):

$$V_2 = S \times \Delta T_2 \quad (7)$$

In this manner, the thermoelectromotive force $V_1$ as a detection signal of the first temperature, and the thermoelectromotive force $V_2$ as a detection signal of the second temperature are obtained.

Subsequently, a process for obtaining the thickness of the adhered layer 6a on the basis of the difference between the first and second temperatures is started.

From equations (3) and (7), the difference between $\Delta T_1$ and $\Delta T_2$ is expressed by the following equation (8):

$$\Delta T_1 - \Delta T_2 = \frac{V_1 - V_2}{S} \quad (8)$$

From equations (1) and (6), the difference between $\Delta T_1$ and $\Delta T_2$ is expressed by the following equation (9):

$$\Delta T_1 - \Delta T_2 = Q \times (R_s - R) \quad (9)$$

From equations (8) and (9), the following equation (10) is obtained:

$$\frac{V_1 - V_2}{S} = Q \times (R_s - R) \quad (10)$$

When equations (2), (3), (4), and (5) are substituted in equation (10) to rearrange it, equation (11), which express the thickness $t_f$ of the adhered layer 6a can be obtained:

$$t_f = t_s \times \frac{\lambda_s}{\lambda_f} \times \frac{L_f}{L_s} \times \frac{W_s}{W_f} \times \frac{V_1 - V_2}{V_2} \quad (11)$$

In equation (11), $\lambda_s$, $L_s$, $W_s$, $t_s$, $\lambda_f$, $L_f$, and $W_f$ are given as known information. Therefore, the thickness $t_f$ of the adhered layer 6a is obtained by detecting the thermoelectromotive forces $V_1$ and $V_2$ as the detection signals of the temperatures.

When a thickness in a liquid during, e.g., plating, is to be measured, electrical insulation with the liquid is taken into consideration, and heat radiation into the liquid is compensated for, thereby measuring the thickness of an adhered layer by plating.

Figure 6:
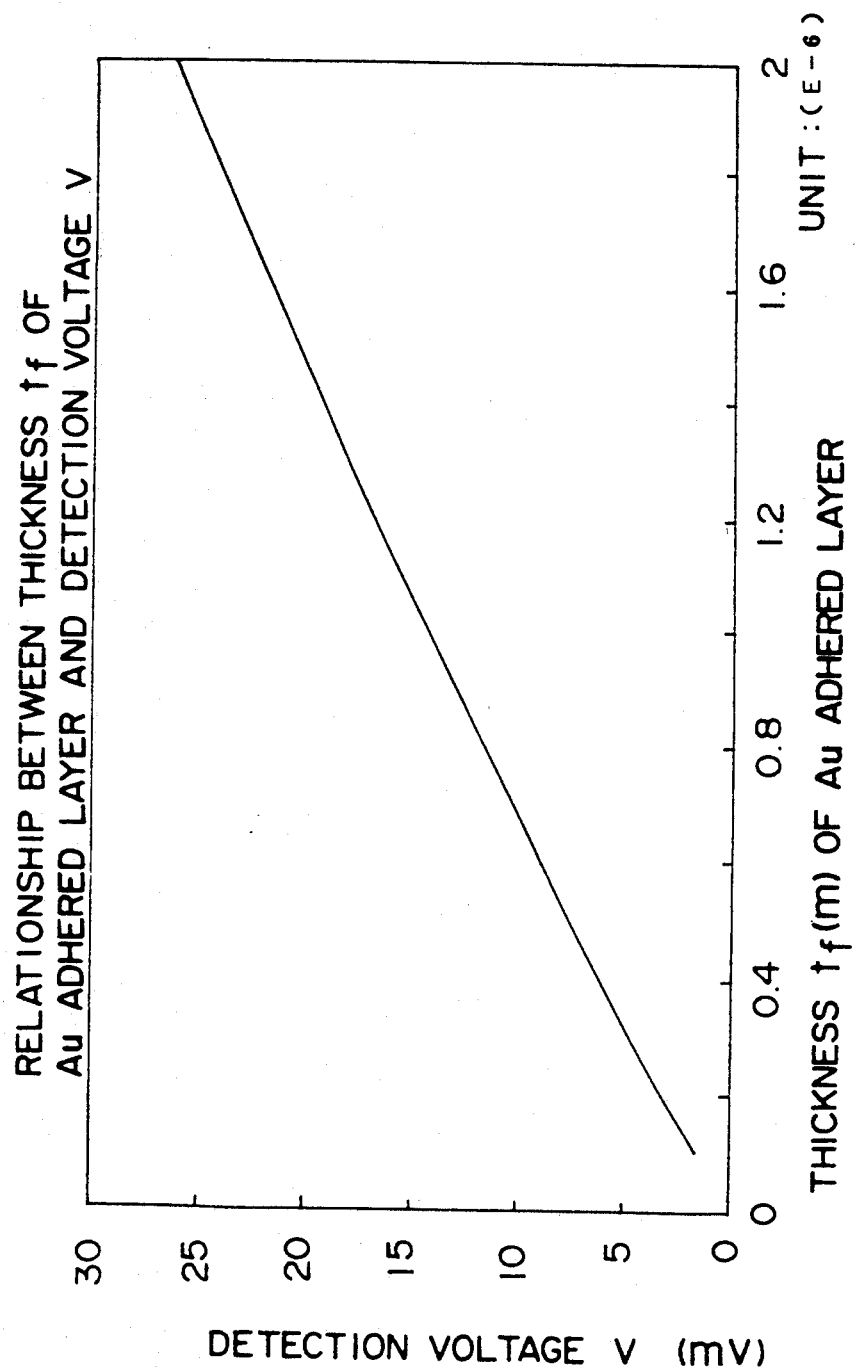
FIG. 6 is a graph showing the relationship between the thickness of an adhered layer and a detected thermoelectromotive voltage.

FIG. 6 is a graph showing the relationship between the thickness $t_f$ of the Au adhered layer 6a and a detected thermoelectromotive force $V_0$. The measurement conditions include that a ceramic substrate having $L_s = 10$ (mm), $W_s = 2$ (mm), and $t_s = 150$ ($\mu$m) is used as the thermally poor conductor substrate 1, the Seebeck coefficient of the thin film thermocouples 31a and 31b is 0.25 (mV/K), and the heat generating amount of the thin film heater 21 is 400 (mW).

The voltage $V_0$ is plotted along the ordinate, and the thickness $t_f$ of the adhered layer 6a is plotted along the abscissa. In this case, the Au adhered layer 6a is adhered on the entire surface opposing the surface on which the thin film heater 21 and the thin film thermocouples 31a and 31b are formed. The detected thermoelectromotive force $V_0$ having good linearity can be obtained as a function of the thickness $t_f$ of the Au adhered layer 6a.

Figure 7:
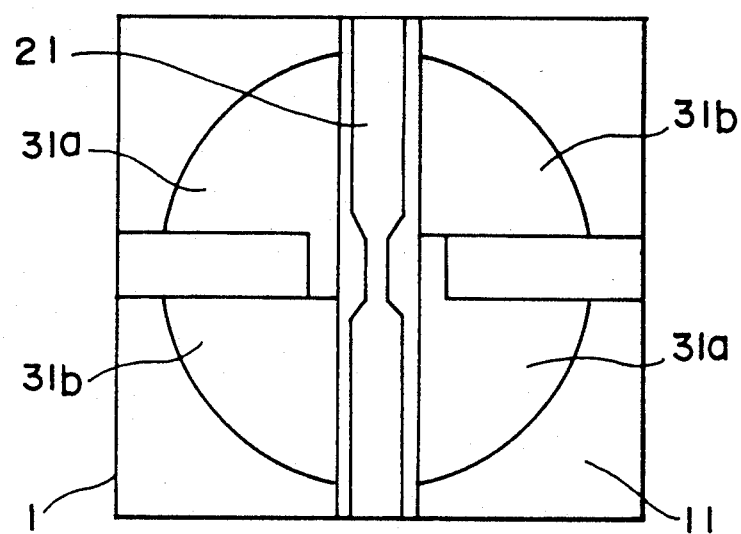
FIG. 7 is a view showing a sensor according to the second embodiment.

FIG. 7 is a view showing another embodiment. In this embodiment, a circularly extending electrode 11 on a peripheral portion is used as the thermostatic portion 6, a thin film heater 21 at the central portion in FIG. 7 is used as the temperature difference setting thin film 2, and two pairs of thin film thermocouples 31a and 31b, which extend in a fan shape, are used as the temperature detection thin film 3. In this case, the thermal resistance is defined between the thin film heater 21 at the central portion and the circularly extending electrode 11 on the peripheral portion. Since the two pairs of thin film thermocouples 31a and 31b are connected in series with each other, a thermoelectromotive force for detecting the temperature is twice that in the above embodiment.

Figure 8:
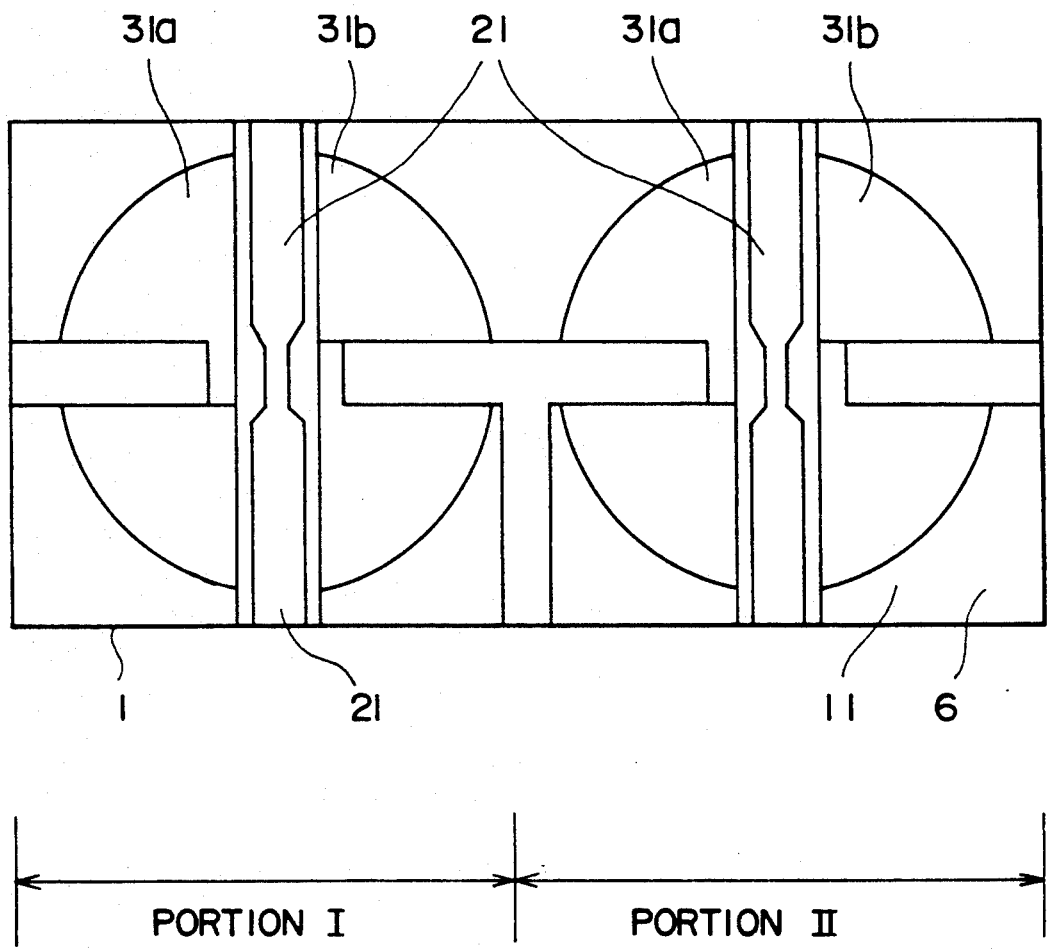
FIG. 8 is a view showing a sensor according to the third embodiment.

FIG. 8 is a further extended embodiment of the embodiment shown in FIG. 7. In this embodiment, the output directions of thermoelectromotive forces of four pairs of thin film thermocouples 31a and 31b have opposite characteristics. Thin film heaters 21 at the central portions have equal heat generating amounts Q. Before an adhered layer is formed, thermoelectromotive forces from the thin film thermocouple pairs 31a and 31b are balanced, and no thermoelectromotive force is output from a thickness sensor as a whole. In contrast to this, when an adhered layer is formed on only one of circular thermal resistive portions (for example, a left portion in FIG. 8 will be referred to as a portion I hereinafter, a right portion in FIG. 8 will be referred to as a portion II hereinafter), only the thermal resistance of the left circular portion in FIG. 8 is decreased. Therefore, the thermoelectromotive force of only the portion I is decreased, and the thermoelectromotive forces of the two portions are unbalanced. As a result, a thermoelectromotive force corresponding to the adhered layer is output from the thickness sensor as a whole.

Figure 9:
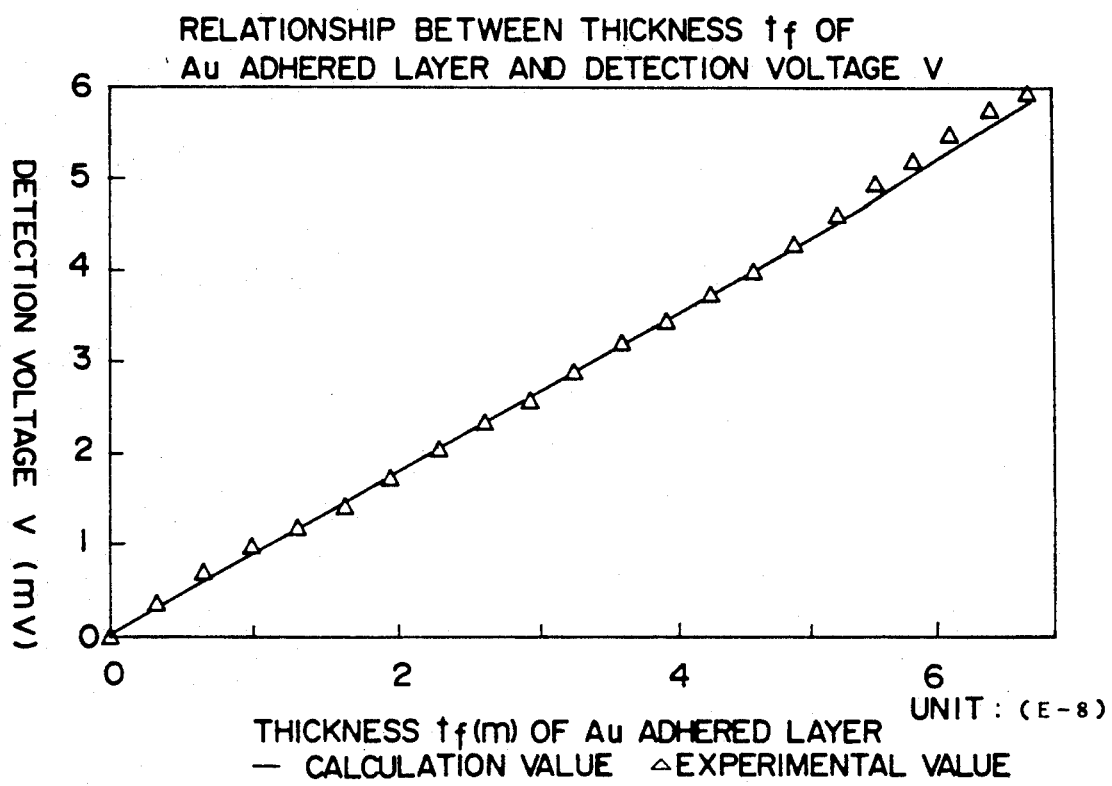
FIG. 9 is a graph showing the relationship between the thickness of an adhered layer and the output heat according to the third embodiment

FIG. 9 shows the relationship between the thickness of an Au adhered layer and the output thermoelectromotive force in the embodiment shown in FIG. 8. A voltage $V_0$ is plotted along the ordinate, and a thickness $t_f$ of the adhered layer is plotted along the abscissa. $\Delta$ indicates experimental values, and a straight line indicates calculation values. As can be seen from FIG. 9, the experimental values and the calculation values present a good coincidence, and the thickness of the Au adhered layer and the output thermoelectromotive force almost have a linear relationship therebetween.

Figure 10A:
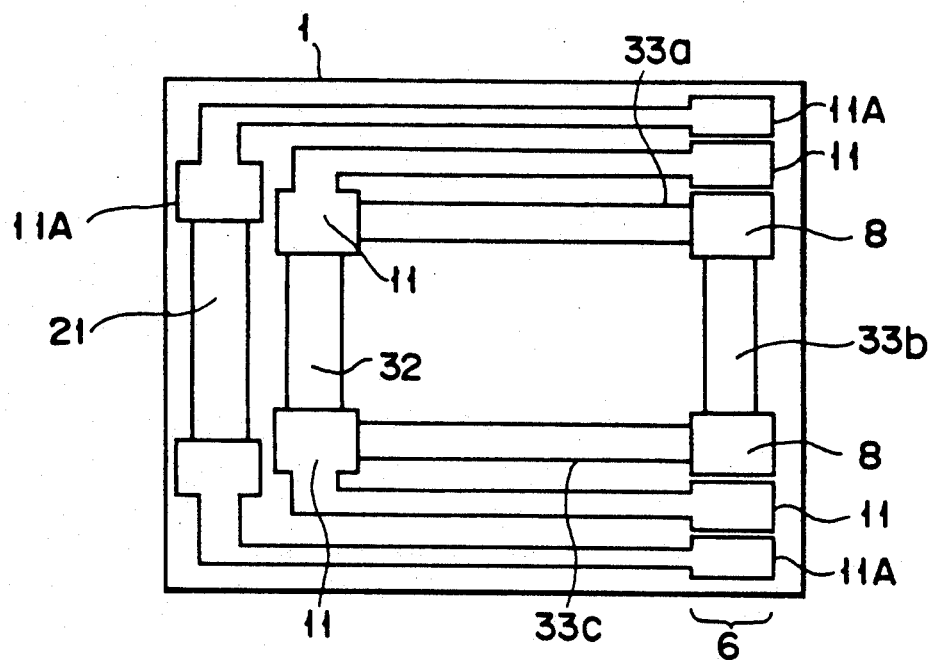
FIGS. 10A and 10B are views showing a sensor according to the fourth embodiment.
Figure 10B:
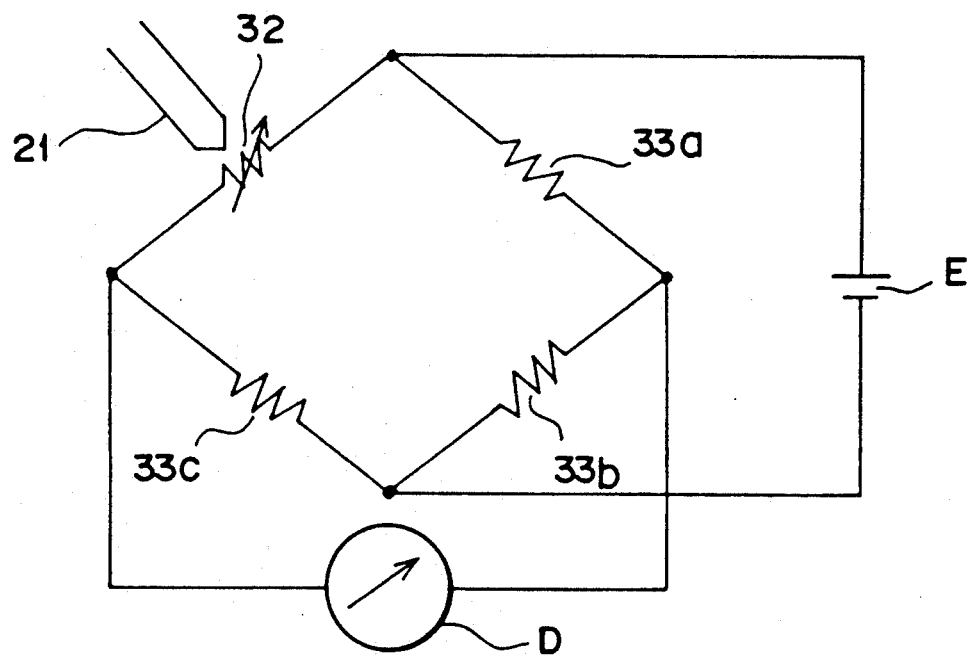

FIGS. 10A and 10B show a structure in which a bridge circuit is integrated on a sensor using a thin film thermistor element 32 and thin film resistors 33a, 33b, and 33c for temperature detection. Note that a thin film heater 21 is used for heating, and a thermostatic portion 6 is located at a side opposite to the thin film heater 21. In FIGS. 10A and 10B, since the thin film thermistor 32 is present at a position closest to the thin film heater 21, when a bias voltage E is applied to this bridge circuit, a voltage corresponding to the temperature is output from the bridge circuit to a detection portion D.

Figure 11:
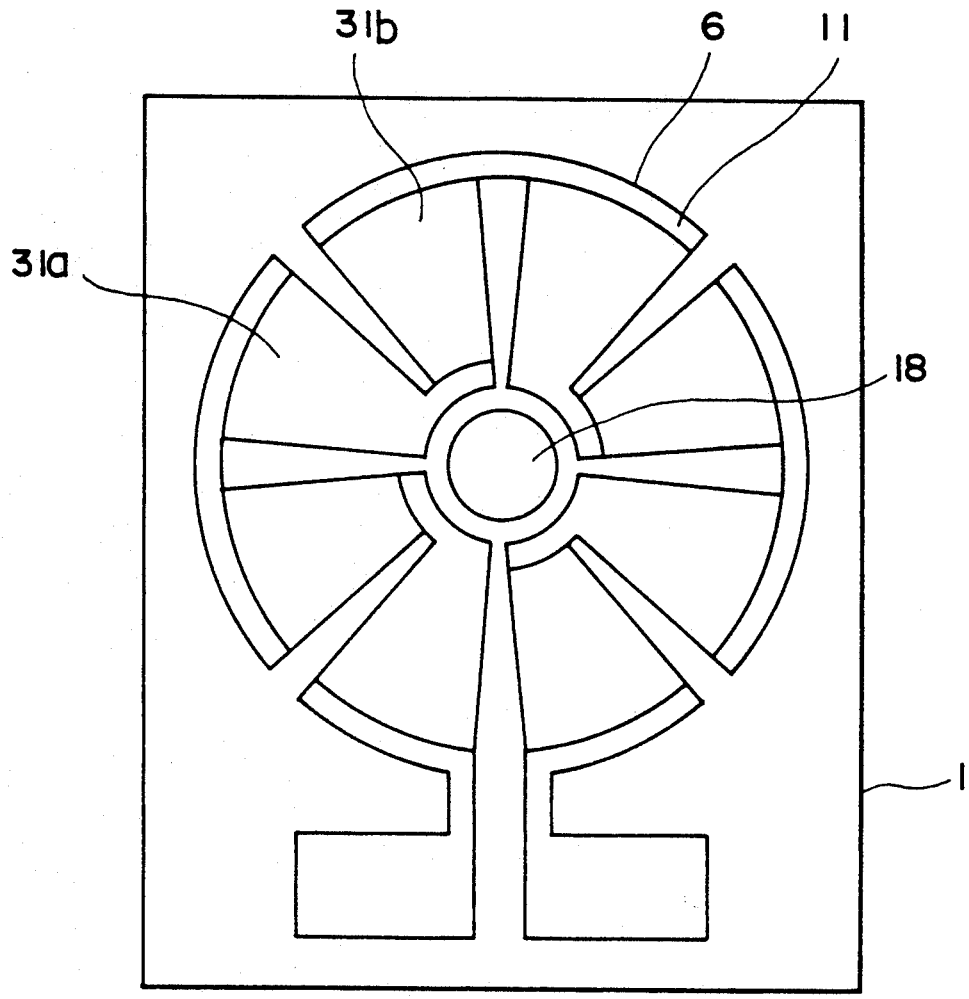
FIG. 11 is a view showing a sensor according to the fifth embodiment.

FIG. 11 shows an embodiment using light for heating. Light is introduced from a portion outside a thickness sensor, is absorbed by a light absorption film 18 at the central portion, and is converted into heat. In temperature detection, a plurality of pairs of thin film thermocouples 31a and 31b are used, and a thermostatic portion 6 corresponds to an electrode 11 portion of a circular peripheral portion. In the embodiment shown in FIG. 11, since light introduced from an external portion is used for heating, the number of wires can be advantageously decreased upon measurement of thickness in, e.g., a vacuum evaporation apparatus.

Figure 12:
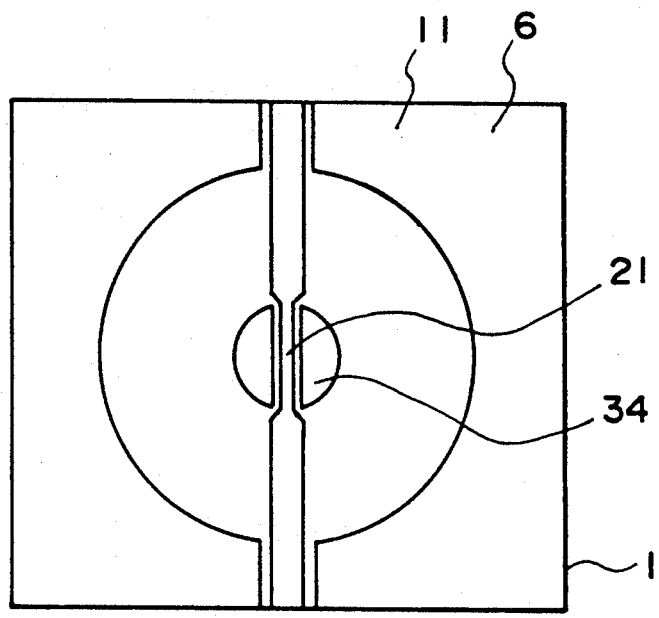
FIG. 12 is a view showing a sensor according to the sixth embodiment.

An embodiment shown in FIG. 12 uses a radiation film 34 such as a black body formed at the central portion to have a circular pattern, and heat radiated from the radiation film 34 is utilized in temperature detection. A thin film heater 21 is used for heating, and a thermostatic portion 6 corresponds to an electrode 11 portion of a circular peripheral portion. In the embodiment shown in FIG. 12, since no wiring is required for temperature detection, the number of wires can be advantageously decreased upon measurement of thickness in, e.g., a vacuum evaporation apparatus.

Figure 13:
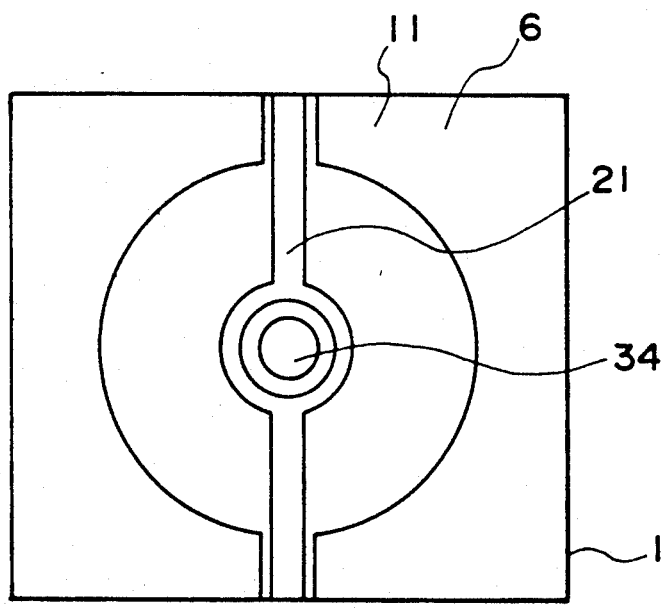
FIG. 13 is a view showing a sensor according to the seventh embodiment.

FIG. 13 shows an embodiment utilizing radiation heat in temperature detection like in the embodiment shown in FIG. 12. A thermostatic portion 6 is also located at an electrode 11 of a circular peripheral portion. However, in the embodiment shown in FIG. 13, since a thin film heater 21 is formed to surround the peripheral portion of the radiation film 34 at the central portion, the temperature of the radiation film 34 can become more uniform and temperature measurement can be more precisely performed as compared to the embodiment shown in FIG. 12.

Figure 14A:
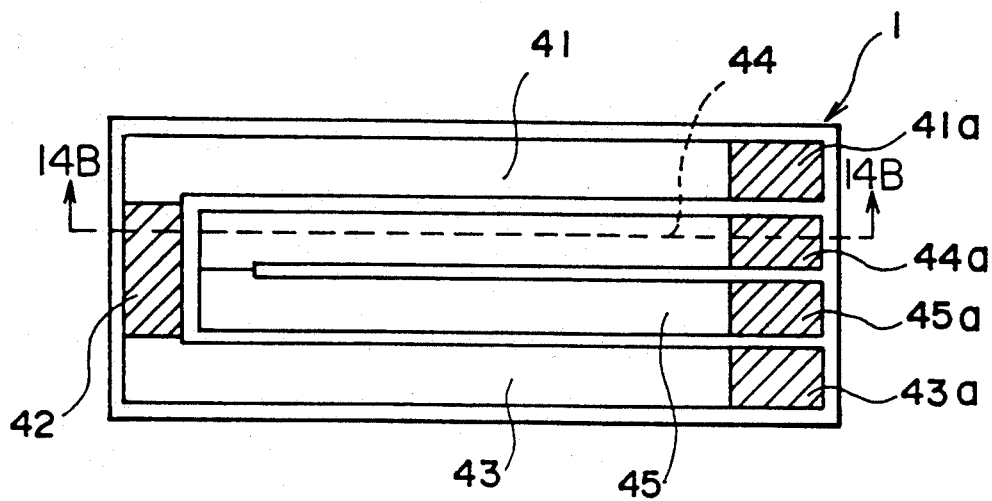
FIGS. 14A and 14B are views showing a sensor according to the eighth embodiment.
Figure 14B:
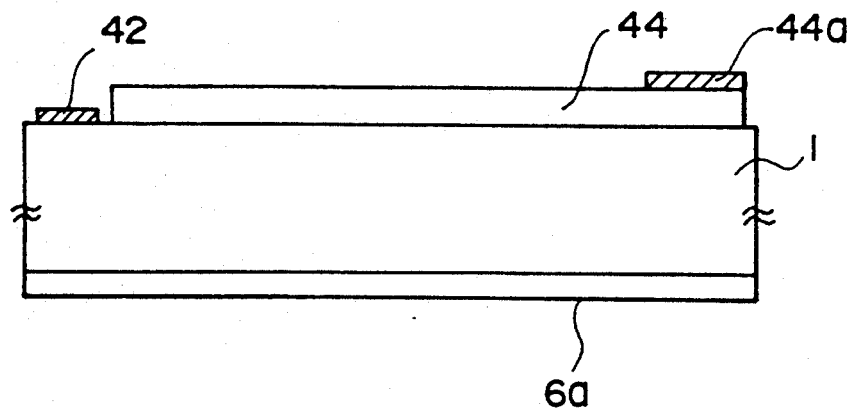

Each of the above-mentioned embodiments has exemplified a case wherein a predetermined position on a substrate is heated. The present invention may be applied to a case wherein a predetermined position of the substrate is not heated but cooled. In an embodiment wherein a predetermined position of the substrate is cooled, as shown in FIGS. 14A and 14B (FIG. 14B being a sectional view taken along line 14B—14B of FIG. 14A), a thin film Peltier effect element formed on a substrate 1 and constituted by an n-type semiconductor thin film 41, a metal thin film 42, and a p-type semiconductor thin film 43 is used in place of a heater, and a current is flowed from the n-type semiconductor thin film 41 toward the p-type semiconductor thin film 43. In this case, cooling (heating when the current flows in the reverse direction) occurs due to the Peltier effect at junction surfaces between the n-type semiconductor thin film 41 and the metal thin film 42, and between the metal thin film 42 and the p-type semiconductor thin film 43. Note that in FIGS. 14A and 14B, reference numerals 44 and 45 denote thin film thermocouples; and 41a, 43a, 44a, and 45a, ohmic electrodes.

In addition, a predetermined position may be cooled by a method other than the Peltier effect, e.g., by blowing a gas or the like cooled within a range, which does not influence a vacuum.

In thickness measurement using such a cooling method, its advantage can be demonstrated when measurement accompanying heat generation is not preferable like in measurement in a cold atmosphere or the like, or when a measurement is performed at a temperature near a high critical temperature.

FIGS. 15A and 15B, and FIGS. 16A and 16B show another embodiment of a sensor according to the present invention, respectively.

Figure 16A:
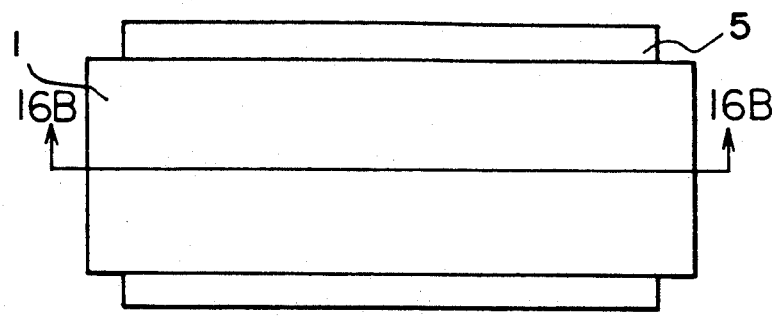
FIGS. 16A and 16B are views showing the sensor of the ninth embodiment connected to a heat sink.
Figure 16B:
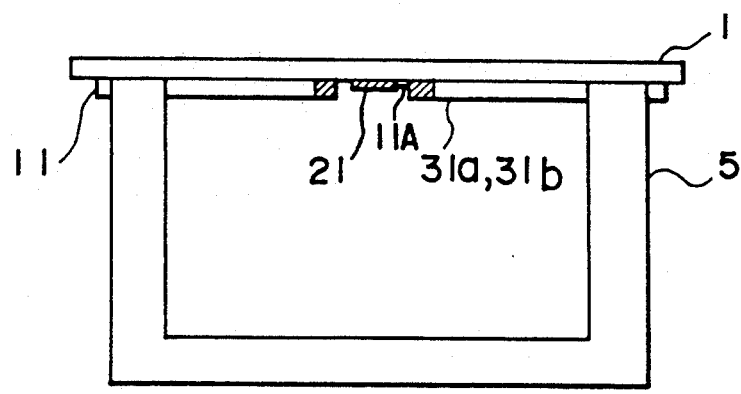

FIG. 15A is a bottom view of a substrate 1, and FIG. 15B is a sectional view taken along a line 15B—15B of FIG. 15A. FIGS. 16A and 16B are views showing a state wherein a heat sink 5 is connected to the structure shown in FIGS. 15A and 15B. FIG. 16A is a top view, and FIG. 16B is a sectional view taken along a line 16B–16B of FIG. 16A. A thin film heater 21 for heating is formed at the central portion of a thermally poor conductor substrate 1, two pairs of thin film thermocouples 31a and 31b are formed near the heater 21, and the two end portions of the substrate 1 are thermally connected to a heat sink 5 formed of a thermally poor conductor. Note that ohmic electrodes 11 and 11A are respectively formed on the thin film heater 21 and the thin film thermocouples 31a and 31b.

Figure 17:
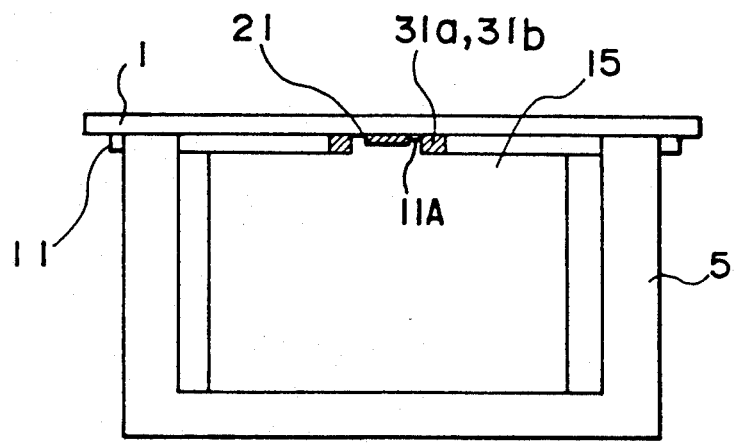
FIG. 17 is a view showing a sensor according to the tenth embodiment.

FIG. 17 shows still another embodiment of a sensor according to the present invention. Thin film heaters 21a and 21b for heating, thin film thermocouples 31a and 31b for temperature detection, and a holding member 15, formed of a thermally poor conductor, for holding a thermally poor conductor substrate 1 are formed on the thermally poor conductor substrate 1 thermally connected to a heat sink 5.

In the embodiment shown in FIGS. 15A and 15B, and FIGS. 16A and 16B, since the thermally poor conductor substrate 1 is not held, this embodiment is effective when bending of the thermally poor conductor substrate 1 due to the specific shape or mass of a substance to be measured can be ignored, or when no gap is formed between the thermally poor conductor substrate 1 and a substance to be measured.

In the embodiment shown in FIG. 17, the thermally poor conductor substrate 1 is held by the holding member 15. For this reason, the embodiment shown in FIG. 17 is effective when bending of the thermally poor conductor substrate 1 due to the specific shape or mass of a substance to be measured cannot be ignored or when a gap is formed between the thermally poor conductor substrate 1 and a substance to be measured in an embodiment having no holding member 15 formed of a thermally poor conductor.

The measurement principle of the embodiments shown in FIGS. 15A and 15B, FIGS. 16A and 16B, and FIG. 17 will be described below with reference to FIG. 18.

Figure 18:
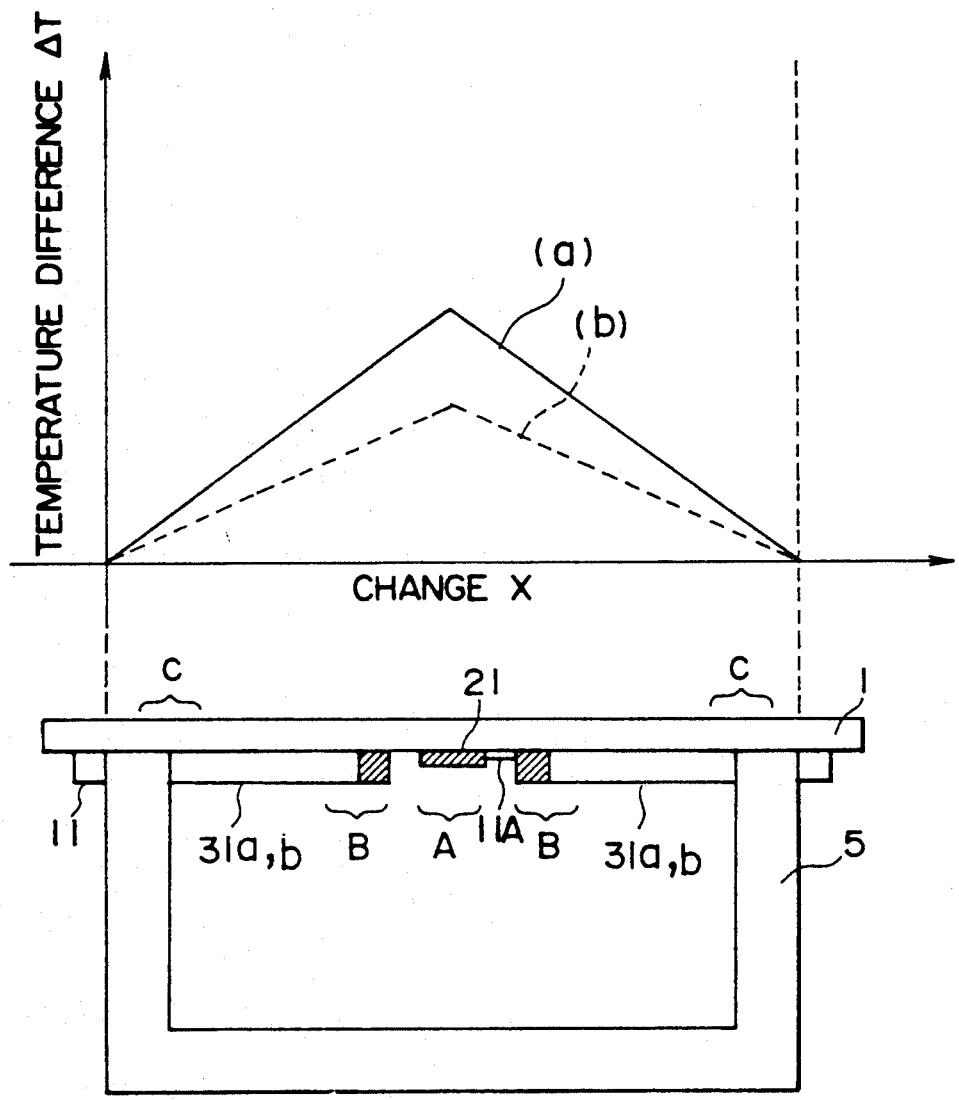
FIG. 18 is a view showing the measurement principle of the ninth embodiment (see A and B)

FIG. 18 shows the flow of heat and the temperature gradient in the substrate in a heated state by the thin film heater 21 for heating, and shows a case wherein a substance to be measured is not in contact with the substrate 1 (a: a solid line in FIG. 18) and a case wherein a substance to be measured is in contact with the substrate 1 (b: a broken line in FIG. 18).

As shown in FIG. 18, the thin film heater 21 for heating is formed at a predetermined position (A in FIG. 18: to be referred to as a heating portion hereinafter) on the thermally poor conductor substrate 1, and the temperature at this position is increased. Desired positions (B in FIG. 18: to be referred to as hot junctions hereinafter) are heated by the thin film heater 21 for heating by a predetermined heat generation amount Q, and their temperatures are increased. In contrast to this, the two end portions (C in FIG. 18: to be referred to as cold junctions hereinafter) are thermally connected to the heat sink 5, and are kept at a constant temperature. In this case, since the cold junctions are thermally connected to the heat sink 5, they maintain a constant temperature regardless of the ON/OFF state of the thin film heater 21. Although such thermostatic portions are necessary for forming cold junctions of the thin film thermocouples 31a and 31b, a temperature gradient (difference) need only be substantially formed in the substrate when a predetermined position on the substrate is heated. In a state wherein the temperatures of the hot junctions as the heated portions are increased, and the cold junctions maintain a constant temperature, a substance to be measured is brought into contact with the substrate 1. At this time, heat flowing from the heated portion A to the cold junctions through only the interior of the substrate partially flows through the interior of the substance to be measured. For this reason, heat can easily flow from the heated portion to the cold junctions, and a temperature difference between the hot and cold junctions changes. At this time, the thermocouples 31a and 31b detect this temperature difference $\Delta T$.

From equations (2), (4), and (5) described above, the temperature difference $\Delta T$ is expressed by the following equation (12):

$$\Delta T = Q \cdot R \qquad (12)$$
$$= Q\left(\frac{1}{R_s} + \frac{1}{R_f}\right)^{-1}$$
$$= \frac{1}{\lambda_s} \cdot \frac{L_s}{W_s t_s} + \frac{1}{\lambda_f} \cdot \frac{L_f}{W_s t_s}$$

As expressed by equation (12), the temperature difference $\Delta T$ corresponds to the thermal conductivity $\lambda_f$, or shape $L_f$, $W_f$, or $t_f$ of this substance to be measured, and when this temperature difference $\Delta T$ is detected, the thermal conductivity of a substance to be measured whose shape is known, or the shape (in particular, the length or thickness) of a substance to be measured whose thermal conductivity is known can be calculated. More specifically, since this temperature difference corresponds to the thermal conductivity of the substance to be measured, when this temperature difference is detected, the thermal conductivity of a substance to be measured whose shape is known, or the shape of a substance to be measured whose thermal conductivity is known can be calculated, as described above. In general, since the width of the substance to be measured is sufficiently larger than the width of the sensor, the influence of the width can be ignored in practice.

When the thermally poor conductor substrate is bent due to the specific shape or mass of a substance to be measured, the holding member 15, formed of a thermally poor conductor, for holding the thermally poor conductor substrate is used. When this holding member is used, formation of a gap between the thermally poor conductor substrate and a substance to be measured caused by the bending can be prevented. As a result, a very large contact thermal resistance generated from this gap, and a measurement error of the thermal conductivity generated by the contact thermal resistance can be prevented. Note that in the embodiment shown in FIG. 17, the thermal conductivity of a substance to be measured whose shape is known, or the shape of a substance to be measured whose thermal conductivity is known can be calculated in consideration of heat flow to the holding member like in the embodiment shown in FIGS. 15A and 15B, and FIGS. 16A and 16B.

Figure 19:
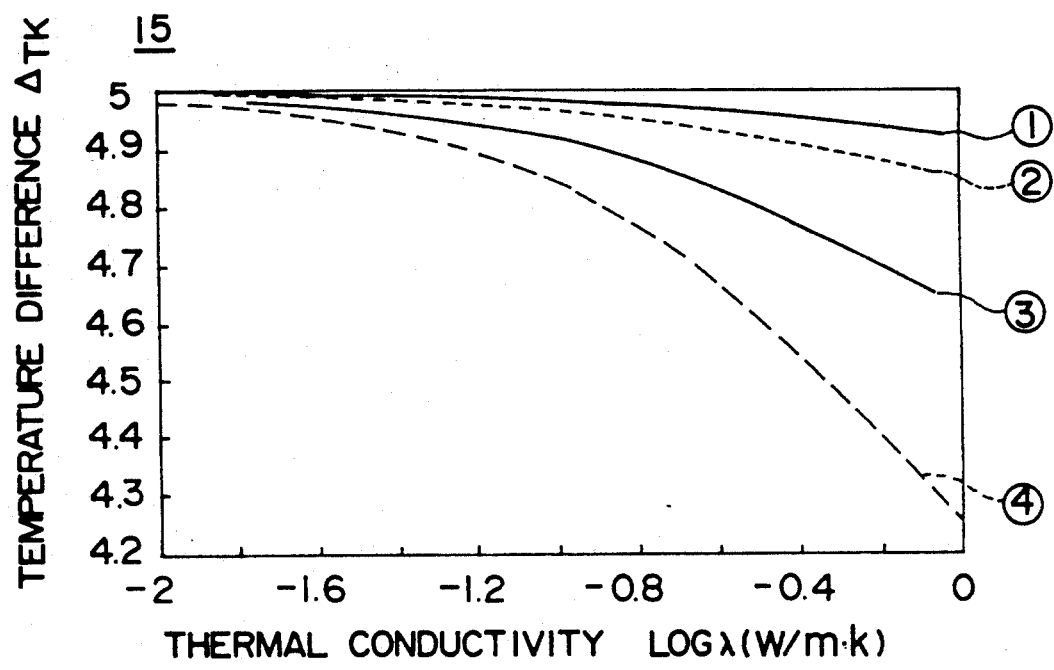
FIG. 19 is a graph showing actual measurement results of the ninth and tenth embodiments.

FIG. 19 shows the relationship between the thermal conductivity $\lambda$ of a substance the temperature difference $\Delta T$ between the hot and cold junctions under a condition that the thermally poor conductor substrate 1 comprises a glass substrate having a length = 10 (mm), a width = 10 (mm), and a thickness = 1 (mm), the thin film heater 21 for heating has a heat generation amount Q = 10 (mW), and a substance to be measured has a thickness t = 5 (mm) and a width W = 10 (mm) in cases wherein the lengths of the substance to be measured are respectively L = 1, 2, 5, and 10 (mm) in the embodiment shown in FIGS. 15A and 15B and FIGS. 16A and 16B. The temperature difference $\Delta T$ (K) is plotted along the ordinate, and the thermal conductivity $\lambda$ (W/m·K) is plotted along the abscissa. The case of L = 1 mm is represented by a curve ①, the case of L = 2 mm is represented by a curve ②, the case of L = 5 mm is represented by a curve ③, and the case of L = 10 mm is represented by curve ④. As shown in FIG. 19, the temperature difference $\Delta T$ corresponds to the thermal conductivity, and when the temperature difference ΔT is detected, the thermal conductivity can be measured. Furthermore, when the length L is changed, the temperature difference ΔT corresponding to the thermal conductivity can be changed. Similarly, the shape of a substance to be measured whose thermal conductivity is known can be measured. The thermal conductivity or shape of the substance to be measured based on the temperature difference can be derived from equation (12) described above. Therefore, when a sensor and an arithmetic circuit are arranged, a thermal conductivity detection apparatus can be constituted, as a matter of course.

In FIG. 19, in a range wherein the thermal conductivity is high, a change in temperature difference between the hot and cold junctions is small. However, since this temperature difference is proportional to the heat generation amount of the thin film heater 21 for heating, when the heat generation amount is increased, the temperature difference can be increased. For this reason, a thin film structure, whose thermal conductivity or shape is difficult to be conventionally measured, can be measured with high precision. In other words, detection sensitivity can be increased. When the number of thin film thermocouple pairs is increased, as needed, the detection sensitivity can be similarly increased.

In the above description, the principle when heat generation amounts $Q_1$ and $Q_2$ are controlled to attain $\Delta T_1 = \Delta T_2$, and a change in heat generation amounts $Q_1$ and $Q_2$ (in practice, these changes can be a change in current to be applied from a power supply to a temperature difference setting thin film) is converted to a change in thermal resistance will be described above. In this case, the sensing system can have an arrangement shown in FIG. 2.

First, $\Delta T_1 = \Delta T_2$ is substituted in equations (1) and (6) to obtain:

$$Q_2 = \frac{R_s}{R} \cdot Q_1 \qquad (13)$$

Then, equation (5) described above is substituted in R of this equation (13) to obtain:

$$Q^2 = \frac{R_2}{\left(\frac{1}{R_s} + \frac{1}{R_f}\right)^{-1}} \cdot Q_1 \qquad (14)$$

Finally, equations (2) and (4) described above are respectively substituted in $R_s$ and $R_f$ of this equation (14) to obtain:

$$Q_2 = \frac{\frac{1}{\lambda_s} \cdot \frac{L_s}{W_s t_s}}{\left(\lambda_s \cdot \frac{W_s t_s}{L_s} + \lambda_s \frac{W_f t_f}{L_f}\right)^{-1}} \cdot Q_1 \qquad (15)$$

In this equation (15), $\lambda_s$, $L_s$, $W_s$, $t_s$, $\lambda_f$, $L_f$, and $W_s$ are given as known information. Therefore, the thickness $t_f$ of the substance to be measured can be calculated by detecting a change $Q_1-Q_2$ (in practice, a change $I_1-I_2$ in current) of the heat generation amounts, and converting the change into a change in thermal resistance.

More specifically, in FIG. 2, the above-mentioned first and second temperature differences $\Delta T_1$ and $\Delta T_2$ detected by the temperature difference detection thin film 203 are stored in the memory 206, and the CPU 209 need only instruct the power supply 204 to change its supply current from $I_1$ to $I_2$ so as to variably control the heat generation amount of the temperature difference setting thin film 202 to attain $\Delta T_1 = \Delta T_2$.

In this case, the differential amplifier 205 shown in FIG. 2 compares temperature difference information from the temperature difference detection thin film 203 and a reference (temperature) signal from the memory 206, and generates a feedback signal to attain $\Delta T_1 = \Delta T_2$. Thus, a change in feedback signal may be detected by the CPU 209 to variably control a supply current from the power supply 204, i.e., the heat amount of the temperature difference setting thin film 202.

Figure 20A:
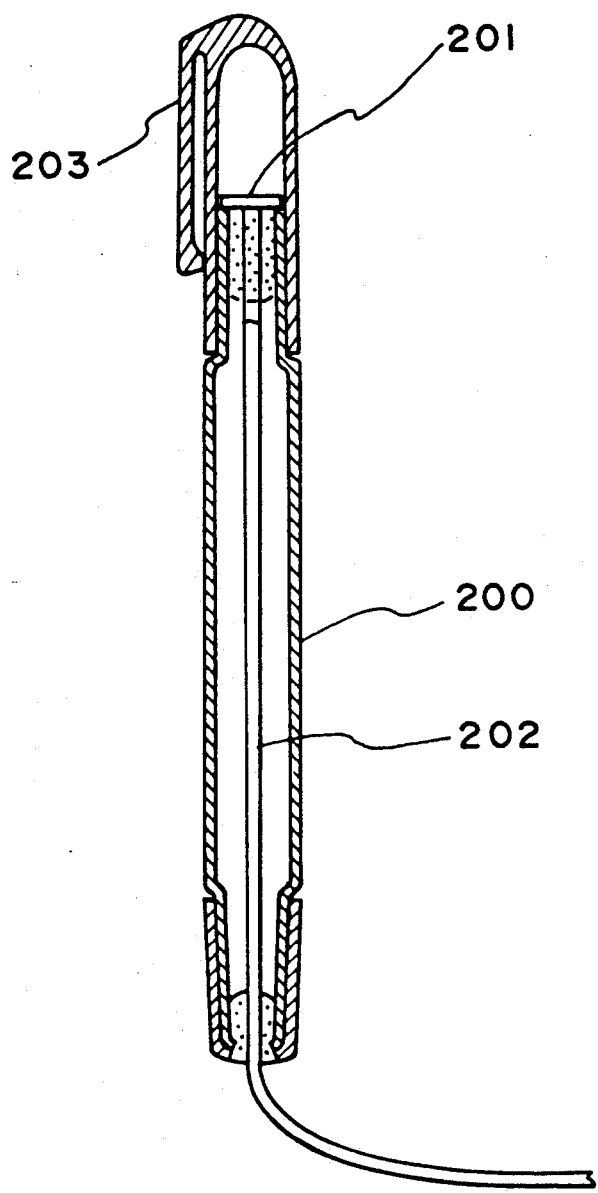
FIGS. 20A, 20B, and 20C are views showing a packaging example of a pen type sensor.

FIG. 20A shows an example wherein the above-mentioned sensor according to the present invention is packaged as a pen type sensor.

More specifically, in this pen type sensor, a sensor 201 (to be described later) is adhered to one end of a cylindrical main body 200 having a diameter of about 10 mm and a thickness of about 150 mm by an epoxy resin, and lead 202 wires (four wires) from heater terminals and thermocouple terminals are extracted from the other end of the main body 200, and are connected to constitute a sensing system, as shown in FIG. 2. A protection cap 203 is detachably arranged on the sensor 201 adhered portion of the main body 200.

Figure 20B:
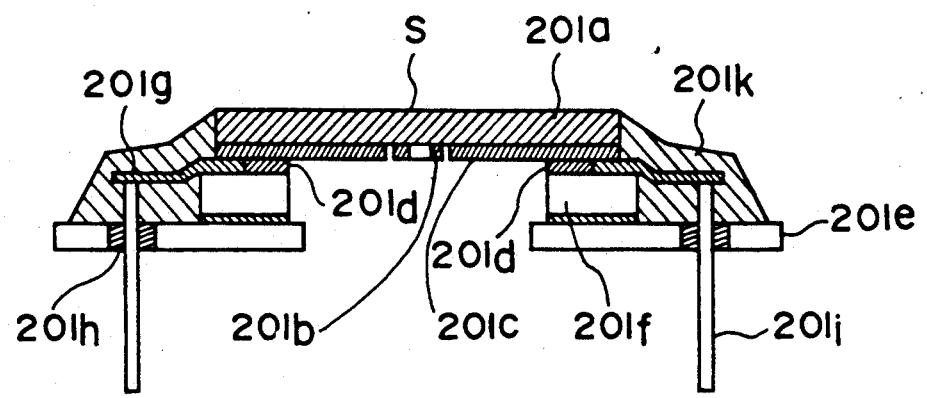
Figure 20C:
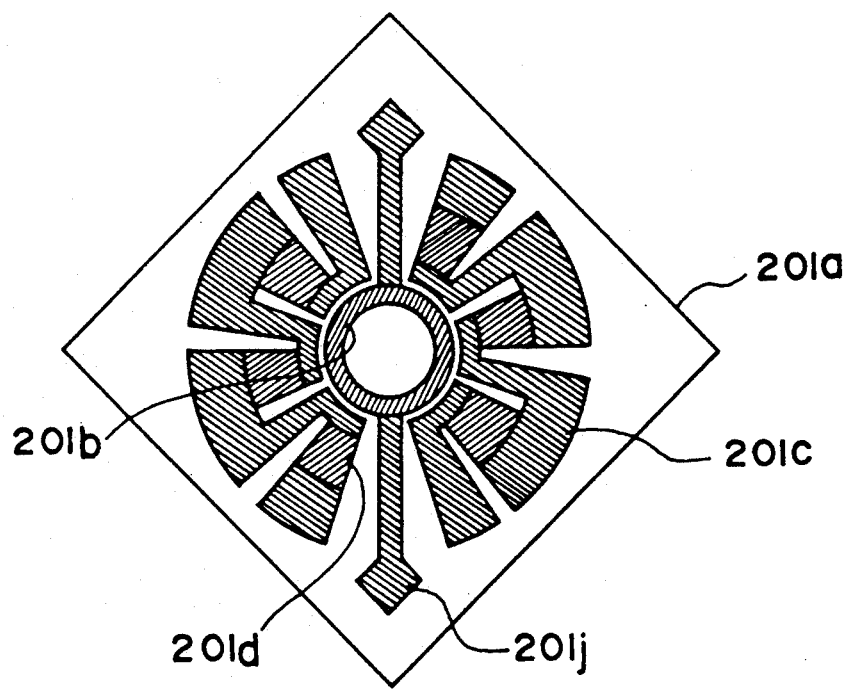

FIGS. 20B and 20C show details of the sensor 201.

More specifically, a thin film heater 201b is formed in a ring shape on the central portion of the lower surface of a substrate 201a, whose upper surface is exposed to serve as a measurement surface S, and fan-shaped metal thin films 201c are formed to surround the thin film heater 201b. Semiconductor thin films 201d for constituting thermocouples are formed at predetermined positions (six positions in FIGS. 20B and 20C) on the fan-shaped metal thin films 201c. The semiconductor thin films 201d are connected to the other end of a ring-shaped heat sink 201f whose one end is attached on a package member 201e. Lead wires 201g extracted from portions between the two end portions of the metal thin films 201c and the heat sink 201f are connected to terminals 201i attached to the two end portions of the package member 201e through insulating seals 201h.

Note that metal thin films 201j joined to the ring-shaped thin film heater 201b, and formed on the substrate 201a are also connected to terminals attached to the package member 201e through insulating seals although not shown.

Protection members 201k for protecting the lead wires 201g and the terminals 201i are formed to extend between the peripheral edge portion of the substrate 201a and the peripheral edge portion of the package member 201e.

The sensing system using the pen type sensor with the above-mentioned arrangement can calculate and measure a desired specific value of a substance to be measured on the basis of substantially the same operation principle as that of the above-mentioned sensors by thermally coupling the measurement surface S of the sensor 201 to the substance to be measured in a state wherein the cap 203 is removed.

Figure 21:
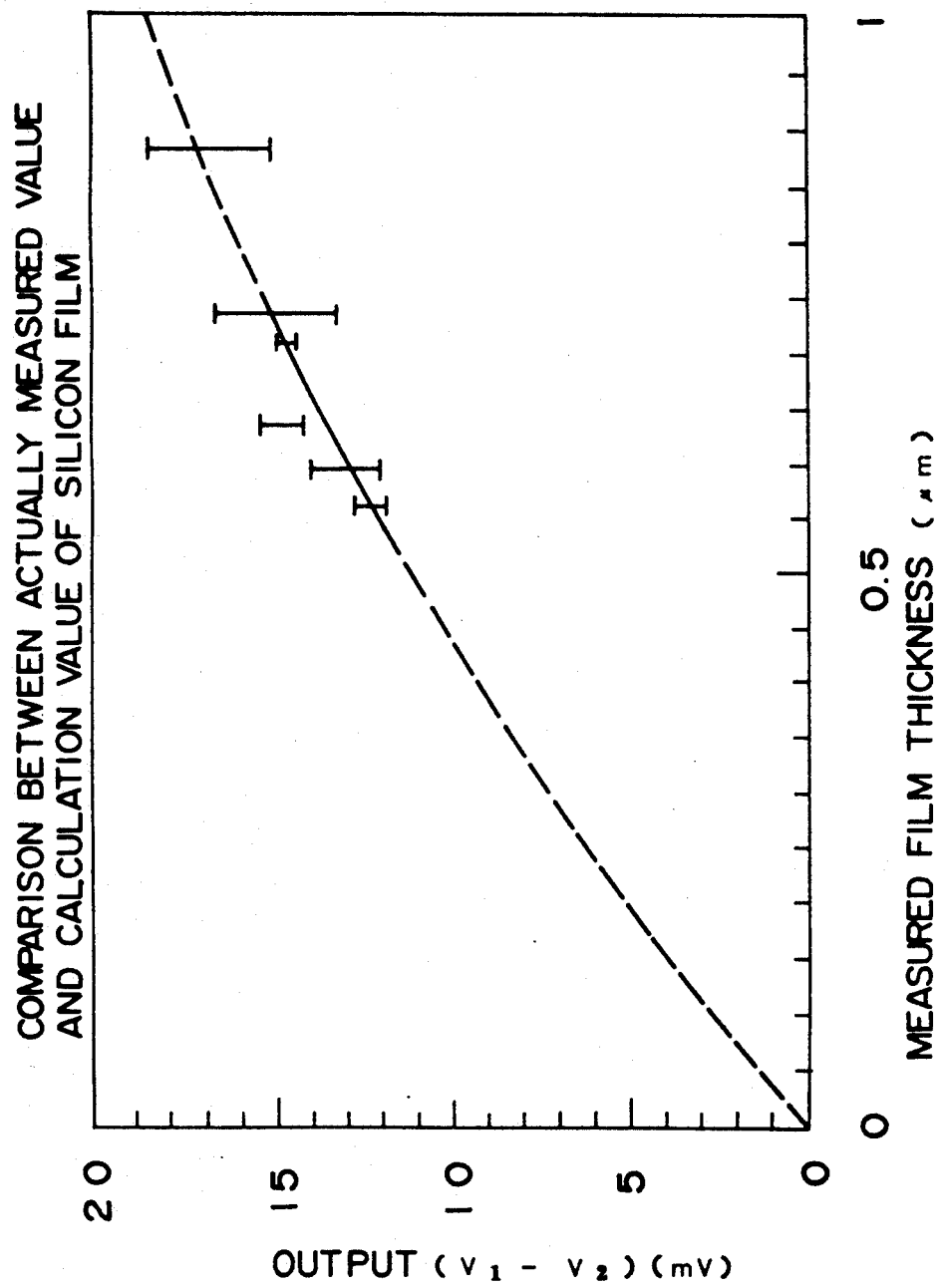
FIGS. 21 and 22 are graphs showing actual measurement results using the pen type sensor.

FIG. 21 shows comparison between an actual measurement value of a silicon film and a calculation value ($V_1-V_2$) as an application of the sensing system using the above-mentioned pen type sensor. FIG. 21 shows that the actual measurement value and the calculation value have a substantially linear relationship therebetween, and thickness measurement using the sensor according to the present invention can be performed with high precision.

Figure 22:
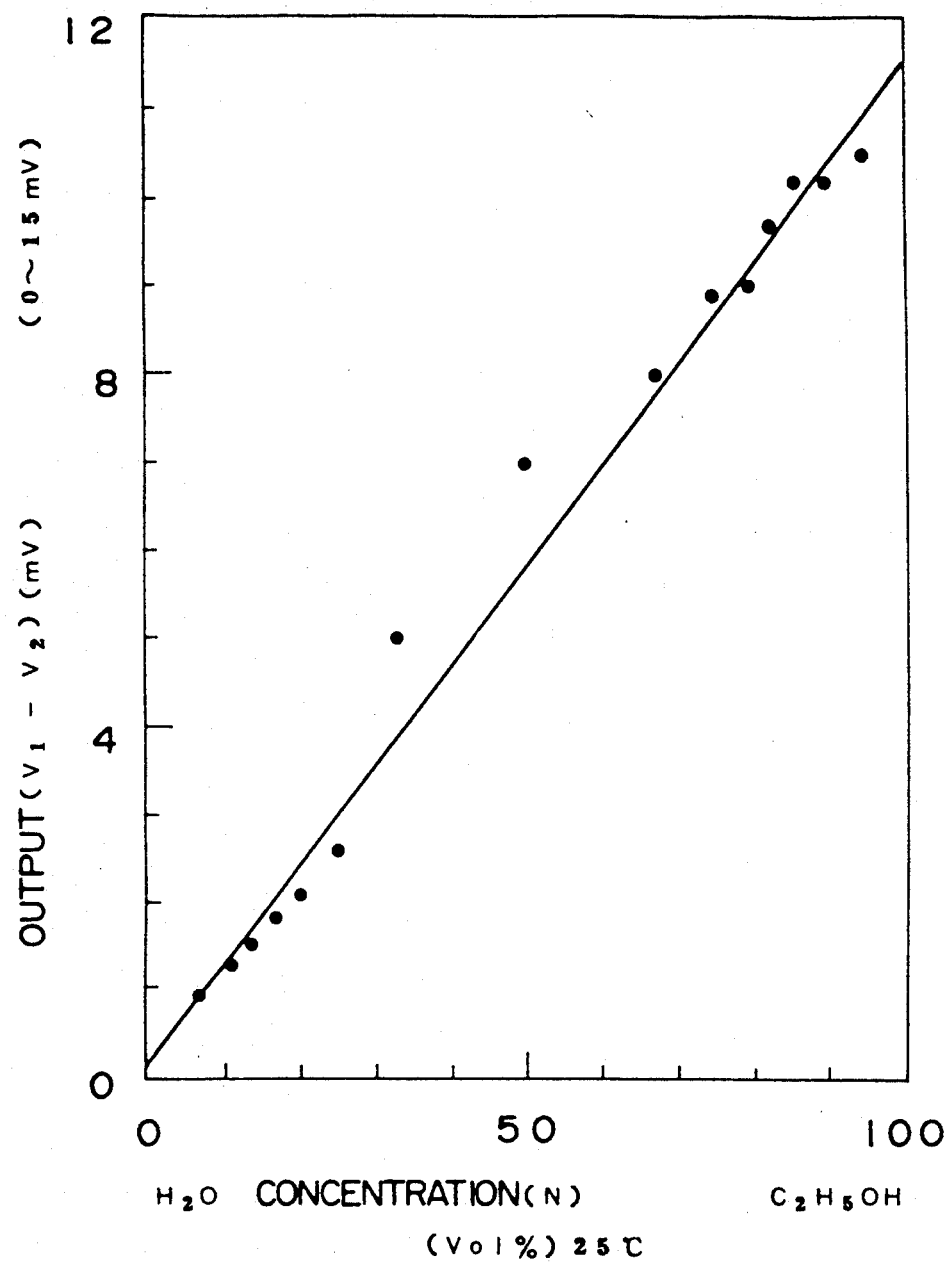

Similarly, FIG. 22 shows concentration dependency of sensor output characteristics of an ethanol/water solution as another application of the sensing system using the pen type sensor. As can be seen from FIG. 22, almost a proportional output voltage can be obtained from 0% to 100%, and the sensor according to the present invention can be applied to a measurement of an alcohol concentration of a liquid such as an alcohol drink, or the like.

The problem of measurement precision (especially, sensitivity) associated with the thickness of a substrate used in each of the above-mentioned sensors, and its solution will be described below.

In the above-mentioned sensor, when a desired position on a substrate is to be heated, and when heat obtained by a heating means is constant, the temperature difference between hot and cold junctions is proportional to the thermal resistance. If the thermal resistance of the substrate is constant, the temperature difference between the hot and cold junctions changes according to the thermal resistance of a substance to be measured connected in parallel with the substrate. However, a thermal resistance $R_V$ of the interior of the substrate in the vertical direction of the substrate is present between the heating means and the substance to be measured. Since this thermal resistance $R_V$ is connected in series with a thermal resistance $R_f$ of the substance to be measured, when the thermal resistance $R_f$ of the substance to be measured is small, a change in thermal resistance $R_f$ of the substance to be measured is considerably smaller than the thermal resistance $R_V$ in the vertical direction of the substrate. For this reason, an output signal does not change largely, and consequently, detection sensitivity is decreased. This problem will be described in detail below.

Figure 23:
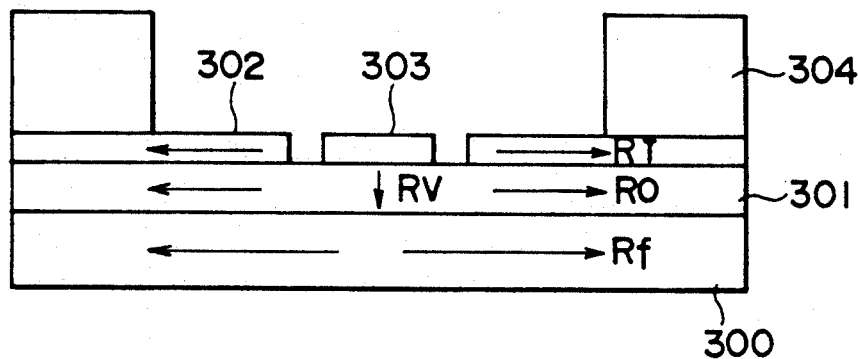
FIG. 23 is a view for explaining measurement sensitivity of a sensor.

As a sensor, a sensor shown in FIG. 23 will be exemplified. In FIG. 23, reference symbol $R_t$ denotes a thermal resistance in a direction of a thermocouple thin film 302; $R_V$, a thermal resistance in the vertical direction of a substrate 301; $R_0$, a thermal resistance in the horizontal direction of the substrate 301; and $R_f$, a thermal resistance of a substance 300 to be measured. Note that reference numeral 303 denotes a thin film heater; and 304, a heat sink.

A total thermal resistance $R_{TH}$ of the overall sensor with the above-mentioned structure is given by:

$$R_{TH} = \frac{1}{\frac{1}{R_t} + \frac{1}{R_0} + \frac{1}{R_V + R_f}} \quad (16)$$

An initial thermal resistance $R_{TH0}$ obtained when the substance 300 to be measured is not thermally coupled to the substrate 301 is given by:

$$R_{TH0} = \frac{R_t \cdot R_0}{R_t + R_0} \quad (17)$$

Therefore, $R_{TH}/R_{TH0}$ representing sensitivity of an output signal according to the thermal resistance of the substance 300 to be measured is given by:

$$\frac{R_{TH}}{R_{TH0}} = \frac{\frac{1}{R_t} + \frac{1}{R_0}}{\frac{1}{R_t} + \frac{1}{R_0} + \frac{1}{R_V + R_f}} \quad (18)$$

For this reason, as the thermal resistance $R_V$ in the vertical direction of the substrate 301 increases, $R_{TH}/R_{TH0}$ approaches unity, resulting in a decrease in sensitivity.

In other words, in order to improve the sensitivity of such a sensor, $R_V$ need only be decreased. Since this $R_V$ is proportional to a thermal conductivity $\lambda_0$ or thickness $T_0$ of the substrate, a substrate having a large thermal conductivity can be used or the thickness of the substrate can be decreased so as to decrease $R_V$.

However, when the thickness of the substrate is decreased too much, a problem of a mechanical strength is posed, and a practical solution is demanded.

Some embodiments of a sensor, which is improved in the above-mentioned respect, i.e., the sensitivity, will be described below.

Figure 24:
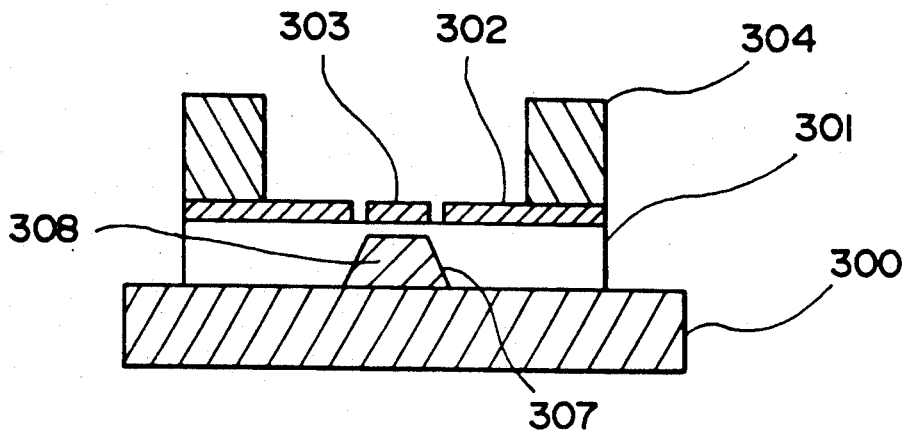
FIGS. 24 and 25 are sectional views showing different embodiments of sensors having improved sensitivity.
Figure 25:
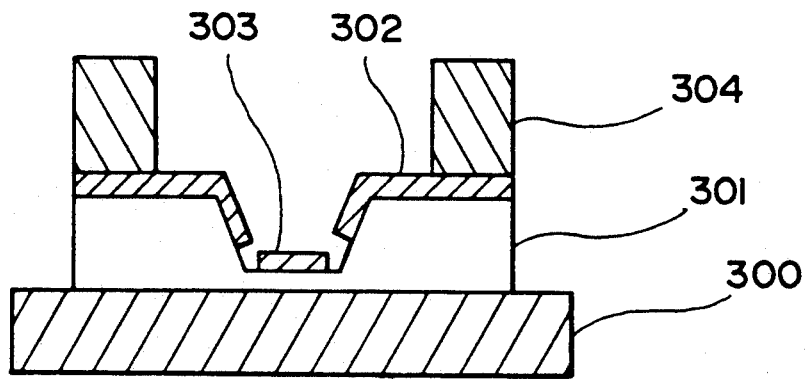

Both sensors shown in FIGS. 24 and 25 are examples wherein a groove 307 is formed to partially decrease the thickness of a substrate 301. Of these sensors, the sensor shown in FIG. 24 has a structure wherein the sensor is thermally coupled to a substance 300 to be measured through a filler 308 such as polysilicon having a low thermal resistance and filled in the groove 307 formed in the substrate 301.

The sensor shown in FIG. 25 has a structure wherein a thin film heater 303 is formed on the bottom portion of the groove 307 formed in the substrate 301, and the sensor is thermally coupled to a substance 307 to be measured at a thin portion of the substrate 301.

The manufacturing process of the sensor shown in FIG. 24 will be described below with reference to FIGS. 26A to 26F.

Figure 26A:
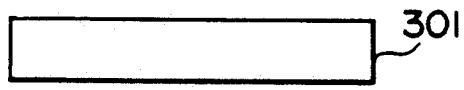
FIGS. 26A to 26F and FIGS. 27A to 27D are sectional views showing steps in the manufacture of the sensors shown in FIGS. 24 and 25, respectively.

(1) A quartz glass substrate 301 having a thickness of 150 μm is prepared. (FIG. 26A)

(2) A 100-nm thick $Si_3N_4$ (silicon nitride) film is deposited on the upper surface of the substrate 301 by CVD.

Figure 26B:
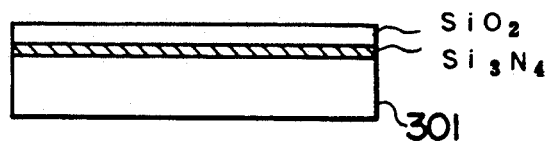

(3) A 10-μm thick $SiO_2$ (silicon oxide) film is deposited on the above-mentioned structure by CVD. (FIG. 26B)

(4) A groove pattern is formed by photolithography at a position on the lower surface of the substrate, which position opposes a thin film heater formation position on the upper surface of the substrate.

Figure 26C:
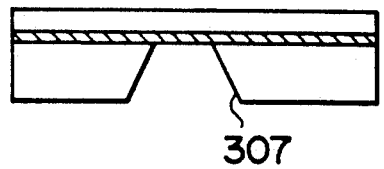

(5) The substrate 301 is etched from its lower surface by an HF-based etching solution to form a groove 307 having a diamond-frame structure. In this case, since the etching speed for the $Si_3N_4$ film is extremely lower than that for the quartz glass substrate 301, etching can be easily stopped up to the interface between the quartz glass substrate and the $Si_3N_4$ film. (FIG. 26C)

(6) The groove 307 is filled with polysilicon by CVD, and a polysilicon film is grown on the entire lower surface of the substrate 301 to have a thickness of 150 μm or more.

Figure 26D:
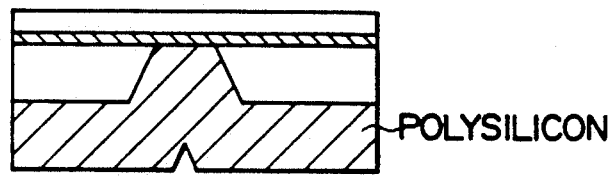

(7) The polysilicon film is polished in correspondence with the non-etched surface of the quartz glass substrate 301 to form an even and smooth surface so as to attain good contact with the substance 300 to be measured. (FIG. 26D)

Figure 26E:
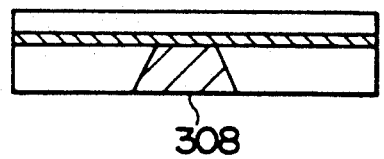
Figure 26F:
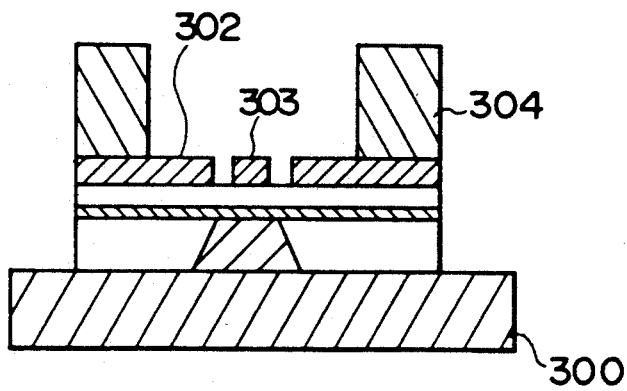

(8) A thin film heater 303 as a heating means, and a thin film thermocouple 302 as a temperature detection means are formed at predetermined positions on the upper surface of the quartz glass substrate 301 by CVD and photolithography. (FIG. 26E).

The manufacturing process of the sensor shown in FIG. 25 will be described below with reference to FIGS. 27A to 27D.

Figure 27A:
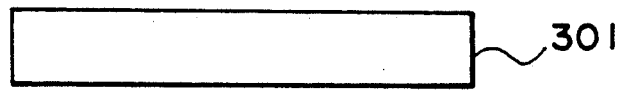

(1) A quartz glass substrate 301 having a thickness of, e.g., 150 $\mu$m is prepared. (FIG. 27A)

Figure 27B:
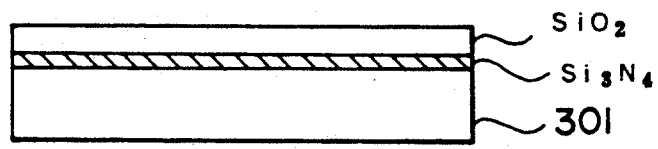

(2) An $Si_3N_4$ (silicon nitride) film is deposited on the lower surface of the substrate 301 by CVD to have a thickness of about 100 nm to 200 nm. (FIG. 27B)

(3) An $SiO_2$ (silicon oxide) film is deposited on the above-mentioned structure by CVD to have a thickness of about 1 $\mu$m to 10 $\mu$m. (FIG. 27B).

(4) A groove pattern is formed by photolithography at a position on the upper surface of the substrate, which position opposes a thin film formation position on the lower surface of the substrate.

Figure 27C:
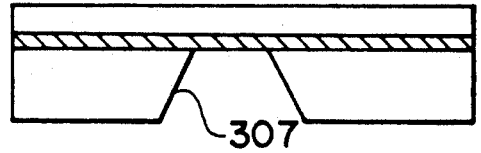
Figure 27D:
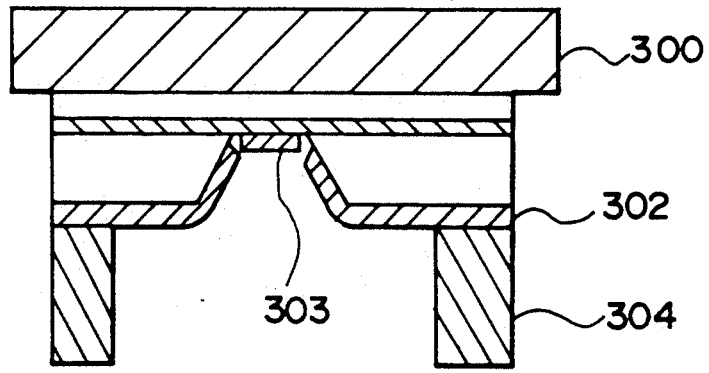

(5) The substrate 301 is etched from the upper surface using an HF-based etching solution to form a groove 307 having a diamond-frame structure. In this case, since the etching speed for the $Si_3N_4$ film is extremely lower than that for the quartz glass substrate 301, etching can be easily stopped up to the interface between the quartz glass substrate 301 and the $Si_3N_4$ film. (FIG. 27C)

(6) A thin film heater 303 as a heating means is formed on the bottom surface of the groove 307 by CVD and photolithography. A thin film thermocouple 302 as a temperature detection means is formed on the inclined side surfaces of the groove 307 and the lower surface of the substrate 301 by anisotropic etching.

Figure 28:
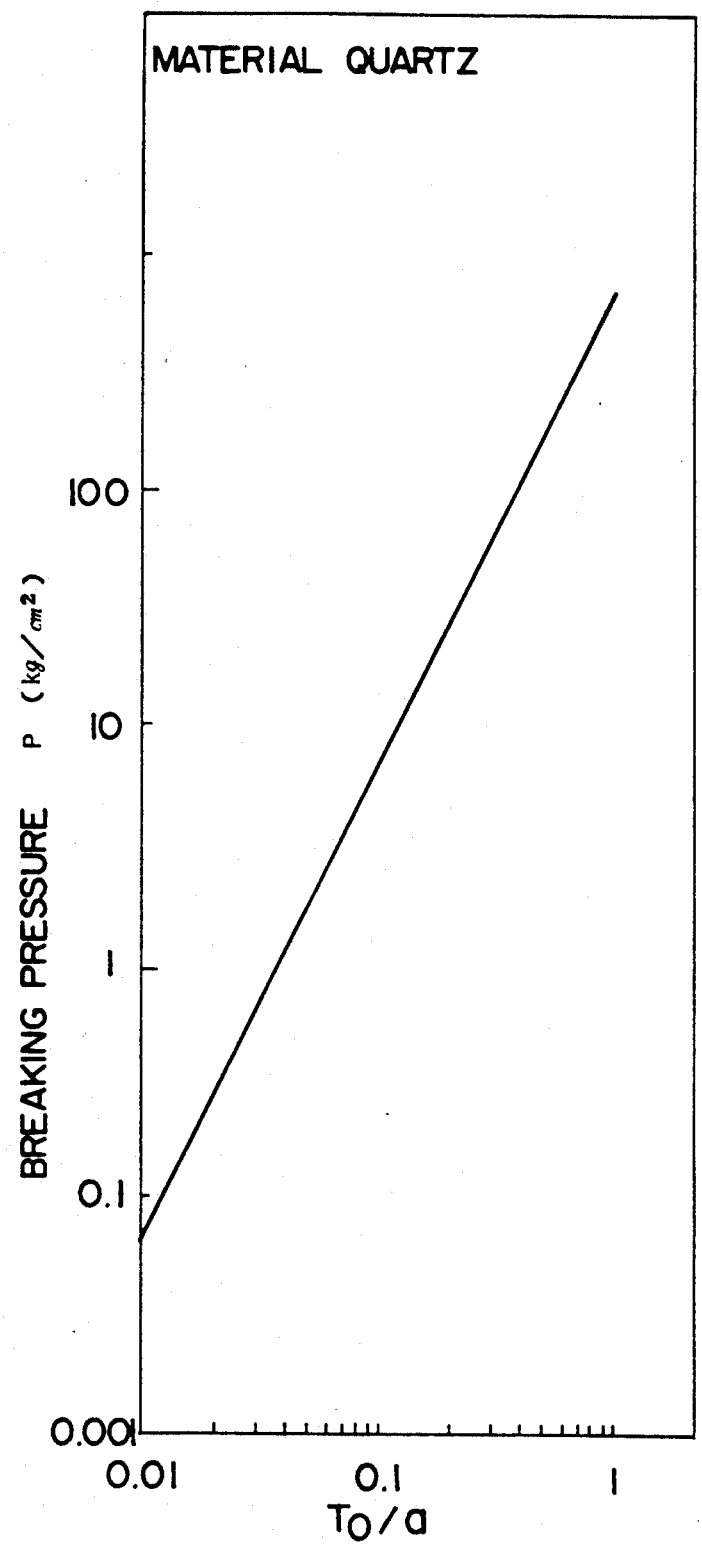
FIGS. 28 to 31 are graphs showing characteristics associated with the sensors shown in FIGS. 24 and 25, respectively.

In each of the sensors shown in FIGS. 24 and 25, the quartz glass substrate 301 has a portion whose thickness is decreased very much by the groove 307. More specifically, the original thickness of the substrate is about 150 $\mu$m, and the thickness of the portion whose thickness is decreased by the groove 307 is about 10 $\mu$m. In this case, since the ratio of the small thickness portion of the substrate to the area of the overall substrate is properly set, a sufficient mechanical strength can be maintained. FIG. 28 shows a calculation result of the mechanical strength of the structure of the element of the present invention on the basis of the fact that the breaking stress of a quartz glass member is 510 kg/cm$^2$. In FIG. 28, the ratio of a thickness (the thickness of a bottom portion of a diamond frame) $T_0$ of a portion formed with the groove in the substrate to a radius a of the bottom portion of the groove is plotted along the abscissa, and the value of a pressure (unit = kg/cm$^2$, to be referred to as a breaking stress hereinafter) at which the sensor substrate is broken is plotted along the ordinate. As can be seen from FIG. 28, when $T_0 = 10$ $\mu$m and a = 300 $\mu$m, the breaking stress is 0.6 kg/cm$^2$, and a sufficient mechanical strength is maintained. As can be seen from FIG. 28, when $T_0/a$ changes within a range between 0.01 and 1, the breaking stress changes within a range between 0.07 to 700 kg/cm$^2$. Thus, when the values of $T_0$ and a are properly set according to an application, a required mechanical strength can be maintained.

In addition, in the sensor shown in FIG. 24, since polysilicon is filled in the groove 307, the mechanical strength can be further increased.

The response speeds of the sensors shown in FIGS. 24 and 25 will be described below with reference to FIG. 29.

Figure 29:
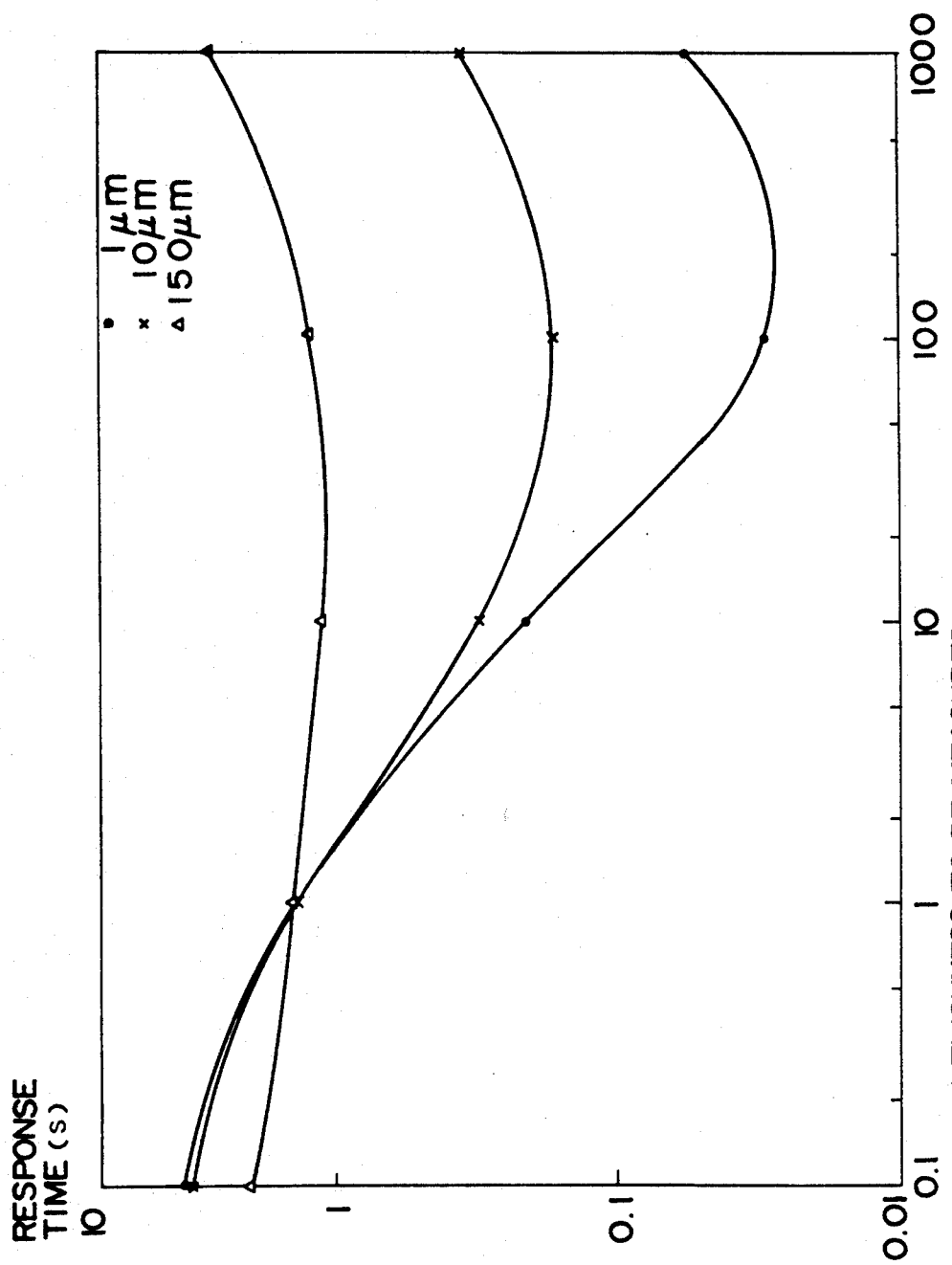

FIG. 29 shows calculation values when an Au film is assumed to be measured by sensors of diamond-frame structures in which the thicknesses of the bottom portions of the grooves are respectively 1 $\mu$m and 10 $\mu$m, and a sensor constituted by a flat substrate having no groove.

As can be seen from FIG. 29, when the film thickness of a substance to be measured is 1 $\mu$m or less, the above-mentioned sensors do not have a large difference. However, as the film thickness of the substance to be measured is increased, the difference among the above-mentioned sensors is gradually increased. When the film thickness of the substance to be measured is 100 $\mu$m, the groove-less sensor has a time constant of 1.35, while the time constants of the sensors of the diamond-frame structures in which the thicknesses of the groove bottom portions are respectively 10 $\mu$m and 1 $\mu$m are greatly decreased to 0.17 and 0.03, thus increasing the response speed.

The degrees of improvement of the sensitivity and response speed of the sensors shown in FIGS. 24 and 25 as compared to the groove-less sensor will be described below with reference to FIG. 30.

Figure 30:
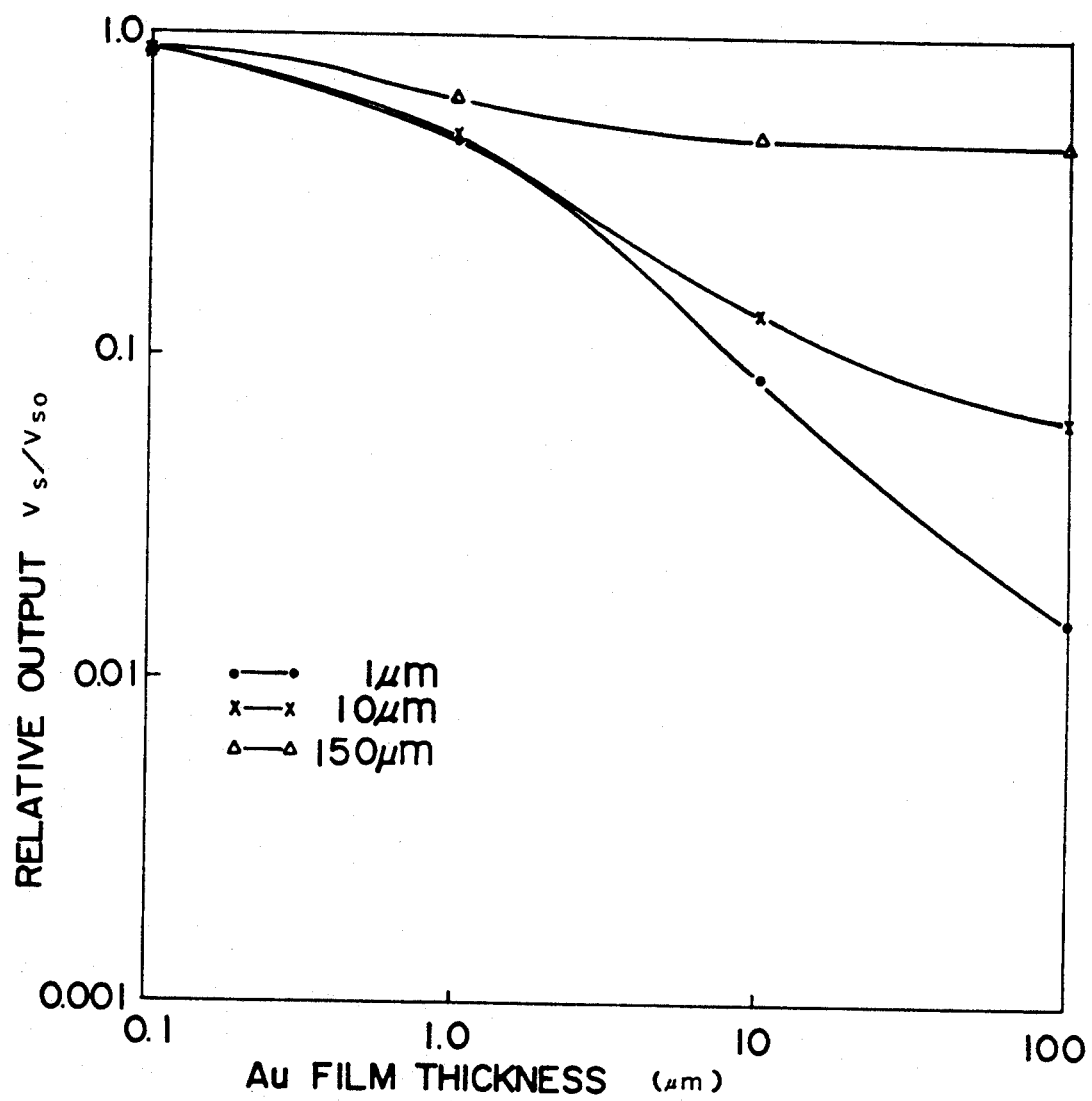

FIG. 30 is a graph showing the relationship between the film thickness of a substance to be measured and the relative output ($V_1/V_2$) of a temperature detection means when an Au film is measured.

The thickness (unit = $\mu$m) of the Au film is plotted along the abscissa, and the relative output, i.e., the ratio of an output voltage $V_2$ obtained when the substance to be measured is coupled to an output voltage $V_1$ obtained when the substance to be measured is not coupled is plotted along the ordinate.

FIG. 30 shows measurement characteristics of a groove-less sensor having $T_0 = 150$ $\mu$m, and sensors which respectively have $T_0 = 1$ $\mu$m and 10 $\mu$m, and in which polysilicon is filled in grooves when the film thickness of a substance to be measured falls within a range between 0.1 $\mu$m and 100 $\mu$m.

As can be seen from FIG. 30, as for the groove-less sensor, the curve is almost flat over the entire measurement range, and the relative output slightly changes from 1 to 0.5. Contrary to this, as $T_0$ is decreased, the output range increases, and the inclination of the curve increases. More specifically, as can be seen from FIG. 30, in the case of the sensors respectively having $T_0 = 1$ $\mu$m and 100 $\mu$m, the relative outputs respectively change within a range between 1 and 0.016 and a range between 1 and 0.065, and the measurement range and sensitivity can be improved.

Figure 31:
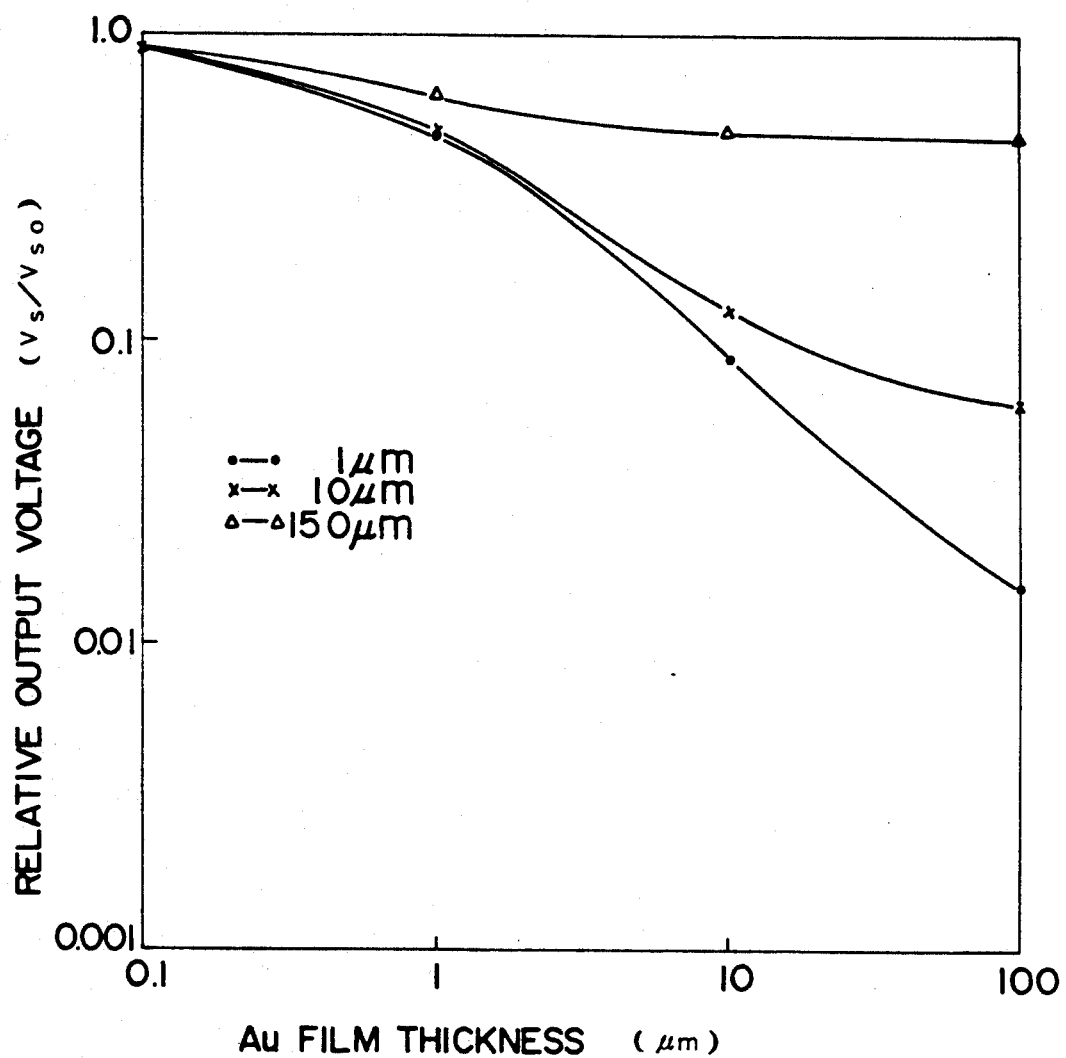

FIG. 31 shows measurement characteristics of a groove-less sensor having $T_0 = 150$ $\mu$m, and sensors which respectively have $T_0 = 1$ $\mu$m and 100 $\mu$m, and in which polysilicon is not filled in grooves. The ordinate and abscissa of FIG. 31 are respectively the same as those shown in FIG. 30. As can be seen from a comparison of FIG. 31 with FIG. 30, both elements with and without a polysilicon filler exhibit similar improvement of characteristics.

As described in detail above, since the sensor heats or cools the substrate, and detects a change in temperature, which depends on a substance to be measured thermally coupled to the substrate, so as to measure a desired specific value of the substance to be measured, a problem that a quartz type film thickness detector generates noise due to a quartz oscillation frequency and a deposition frequency upon measurement of the thickness of an evaporated film can be solved, and precise measurement can be performed.

Since the sensor of the present invention comprises the temperature difference setting thin film and the temperature detection thin film formed on the substrate, a compact structure can be easily attained by using, e.g., a semiconductor thin film technique. For this reason, the sensor can be set at a position having an optimal measurement condition, a multi-point measurement upon vacuum evaporation can be performed, and a larger amount of substance to be evaporated can be evaporated.

The sensor of the present invention can be manufactured at very low cost by using, e.g., a semiconductor thin film technique despite its high performance.

Furthermore, since the sensor of the present invention has a simple measurement principle, various problems do not easily occur.

Since the sensor according to the present invention directly calculates thermal conductivity on the basis of a change in temperature difference, a conventional problem that the thermal conductivity of a substance to be measured cannot be measured unless the density and specific heat values of the substance to be measured are obtained in advance can be solved.

A thermal conductivity detection element according to the present invention has a heating means and a temperature detection means, which are formed on a thermally poor conductor substrate by a semiconductor process, e.g., photolithography, and these means are arranged on a single plane of a single substrate. As a result, the following effects can be derived.

(1) An integrated and compact structure of the sensor can be attained.

(2) Since the sensor element according to the present invention can measure the thermal conductivity or shape of a substance to be measured by only coupling the substance to be measured to the substrate, a conventional problem that the thermal conductivity of a substance to be measured cannot be measured unless a measurement sample of a substance to be measured is manufactured for a measurement can be solved, and a non-destructive measurement can be realized.

(3) Furthermore, since the sensor according to the present invention can solve a conventional problem that the thermal conductivity of a substance to be measured cannot be measured unless the substance to be measured is sandwiched between a high-thermal conductivity substrate and a low-thermal conductivity substrate, i.e., the substance to be measured is limited, and can perform an easy thermal conductivity measurement.

For this reason, objects to be measured can be extended to, e.g., constructions, gas piping systems, structures, and the like, and the degree of progress of deterioration or corrosion of such objects can be inspected. In addition, the thickness of an asphalt, the alcohol concentration in water, and the like can be measured. Thus, the field of objects to be measured can be expanded to a very wide one.

Therefore, according to the present invention, a sensor device, which has features, for example, can easily realize a compact and integrated structure, allows an easy measurement, is not easily influenced by high-frequency noise, and is inexpensive, and which can measure a specific value such as the thickness and thermal conductivity of a substance to be measured, the liquid concentration, and the like can be provided.

According to the present invention, a sensing device, which has features, for example, can easily realize a compact and integrated structure, allows an easy measurement, is not easily influenced by high-frequency noise, and is inexpensive, and which can measure a specific value such as the thickness and thermal conductivity of a substance to be measured, the liquid concentration, and the like can be provided.

According to the present invention, a sensing method, which has features, for example, can easily realize a compact and integrated structure, allows an easy measurement, is not easily influenced by high-frequency noise, and is inexpensive, and which can measure a specific value such as the thickness and thermal conductivity of a substance to be measured, the liquid concentration, and the like can be provided.

Furthermore, according to the present invention, a sensor, which can increase the response speed, and can improve measurement precision, can be provided.

INDUSTRIAL APPLICABILITY

Since a sensing system for measuring a specific value of a substance to be measured using a change in thermal resistance according to the present invention can easily measure a specific value such as the thickness and thermal conductivity of a substance to be measured, the liquid concentration, and the like with high precision by a compact structure, it can be utilized in a wide application range including not only for desired specific values having thermal dependency in objects to be measured in a wide range such as liquids, solids, constructions, and the like, but also estimation of the degree of progress of deterioration or corrosion.

We claim:

1. A sensor comprising:
   a heat sink;
   a substrate at least a portion of which can be thermally coupled to a substance to be measured, another portion of which is thermally coupled to said heat sink, and which is formed of a thermally poor conductor;
   a temperature difference setting thin film formed on said substrate to provide a temperature difference to said substrate;
   a temperature difference detection thin film formed on said substrate to detect a change in temperature difference provided by said temperature difference setting thin film;
   first electrode means, formed on said substrate, for supplying a predetermined electrical power to said temperature difference setting thin film; and
   second electrode means, formed on said substrate, for outputting an output from said temperature difference detection thin film, and
   wherein a change in temperature difference provided to said substrate before and after the substance to be measured is thermally coupled to said substrate is converted into a change in thermal resistance of said substrate, and the change in thermal resistance of said substrate is output as a temperature difference information signal for calculating a desired specific value of the substance to be measured.

2. A sensor according to claim 1, wherein said temperature difference setting thin film includes a thin film heater element.

3. A sensor according to claim 1, wherein said temperature difference setting thin film includes a thin film Peltier effect element.

4. A sensor according to claim 1, wherein a groove is formed in said substrate to decrease a thickness of a portion, to be thermally coupled to the substance to be measured, of said substrate, and said substrate can be thermally coupled to the substance to be measured through a filler layer filled in the groove and formed of a material having a higher thermal conductivity than said substrate.

5. A sensor according to claim 1, wherein a groove is formed in said substrate to decrease a thickness of a portion, to be thermally coupled to the substance to be measured, of said substrate, said temperature difference setting thin film is formed on a bottom portion of the groove, and said temperature difference detection thin film is formed to extend over side surfaces of the groove and one surface of said substrate contiguous with the side surfaces, so that said substrate can be thermally coupled to the substance to be measured through the small-thickness portion from the other surface of said substrate.

6. A sensing device comprising:
a heat sink;
a substrate at least a portion of which can be thermally coupled to a substance to be measured, another portion of which is thermally coupled to said heat sink, and which is formed of a thermally poor conductor;
temperature difference setting means for providing a temperature difference to said substrate;
temperature difference detection means for detecting a change in temperature difference provided by said temperature difference setting means;
temperature difference/thermal resistance conversion means for converting, into a change in thermal resistance of said substrate, the change in temperature difference detected by said temperature difference detection means before and after the substance to be measured is thermally coupled to said substrate; and
specific value calculation means for calculating a desired specific value of the substance to be measured according to the change in thermal resistance converted by said temperature difference/thermal resistance conversion means, and known information of the substance to be measured.

7. A sensing device according to claim 6, wherein when the known information of the substance to be measured is a predetermined information group including a thermal conductivity of the substance to be measured, said specific value calculation means calculates a thickness of the substance to be measured as the desired specific value of the substance to be measured.

8. A sensing device according to claim 6, wherein when the known information of the substance to be measured is a predetermined information group including a thickness of the substance to be measured, said specific value calculation means calculates a thermal conductivity of the substance to be measured as the desired specific value of the substance to be measured.

9. A sensing device according to claim 6, wherein said temperature difference setting means includes means for maintaining a predetermined position on said substrate at a constant temperature.

10. A sensing device according to claim 6, wherein said temperature difference/thermal resistance conversion means includes control means for variably controlling a heat amount of said temperature difference setting means so as to equalize the changes in temperature difference detected by said temperature difference detection means before and after the substance to be measured is thermally coupled to said substrate, and means for converting a change in heat amount by said control means into the change in thermal resistance of said substrate.

11. A sensing device according to claim 6, wherein said temperature difference/thermal resistance conversion means includes means for comparing temperature difference information detected by said temperature difference detection means with a reference temperature signal, and generating a feedback signal, control means for variably controlling a heat amount of said temperature difference setting means according to the feedback signal so as to equalize the changes in temperature difference detected by said temperature difference detection means before and after the substance to be measured is thermally coupled to said substrate, and means for converting a change in heat amount by said control means into the change in thermal resistance of said substrate.

12. A sensing method comprising the steps of:
setting a temperature difference in a substrate at least a portion of which can be thermally coupled to a substance to be measured;
detecting a first temperature difference in said substrate in a state wherein the substance to be measured is not thermally coupled to said substrate;
thermally coupling said substrate to the substance to be measured;
detecting a second temperature difference in said substrate in a state wherein the substance to be measured is thermally coupled to said substrate;
converting the first and second temperature differences into a thermal resistance of said substrate; and
calculating a specific value of the substance to be measured according to the converted thermal resistance and known information of the substance to be measured.

13. A sensing method according to claim 12, wherein when the known information of the substance to be measured is a predetermined information group including a thermal conductivity of the substance to be measured, a thickness of the substance to be measured is calculated as the desired specific value of the substance to be measured.

14. A sensing method according to claim 12, wherein when the known information of the substance to be measured is a predetermined information group including a thickness of the substance to be measured, a thermal conductivity of the substance to be measured is calculated as the desired specific value of the substance to be measured.

15. A sensing method according to claim 12, wherein said substrate includes means for maintaining a predetermined position thereof at a constant temperature.

16. A sensing method according to claim 12, wherein the conversion step includes the step of variably controlling a heat amount applied to said substrate so as to equalize the changes in temperature difference detected before and after the substance to be measured is thermally coupled to said substrate, and the step of converting a change in heat amount into a change in thermal resistance of said substrate.

17. A sensing method according to claim 12, wherein the conversion step includes the step of comparing temperature difference information detected in the steps of detecting the first and second temperature differences with a reference temperature signal, and generating a feedback signal, the step of variably controlling a heat amount applied to said substrate according to the feedback signal so as to equalize the changes in temperature difference detected before and after the substance to be measured is thermally coupled to said substrate, and the step of converting a change in heat amount into a change in thermal resistance of said substrate.

18. A sensor according to claim 1, wherein said temperature difference detection thin film includes a thin film thermocouple element.

19. A sensor according to claim 1, wherein said temperature difference detection thin film includes a thin film thermistor element.

20. A sensor according to claim 1, wherein said sensor is packaged as a pen type sensor.

* * * * *